United States Patent
Ohmori et al.

(10) Patent No.: US 12,220,173 B2
(45) Date of Patent: Feb. 11, 2025

(54) SLIT-LAMP MICROSCOPE AND OPHTHALMIC SYSTEM

(71) Applicant: TOPCON CORPORATION, Tokyo (JP)

(72) Inventors: Kazuhiro Ohmori, Tokyo (JP); Yasufumi Fukuma, Wako (JP); Satoshi Yamamoto, Saitama (JP)

(73) Assignee: TOPCON CORPORATION, Tokyo (JP)

( * ) Notice: Subject to any disclaimer, the term of this patent is extended or adjusted under 35 U.S.C. 154(b) by 1200 days.

(21) Appl. No.: 16/976,782

(22) PCT Filed: Mar. 13, 2019

(86) PCT No.: PCT/JP2019/010136
§ 371 (c)(1),
(2) Date: Aug. 31, 2020

(87) PCT Pub. No.: WO2019/176973
PCT Pub. Date: Sep. 19, 2019

(65) Prior Publication Data
US 2021/0038076 A1    Feb. 11, 2021

(30) Foreign Application Priority Data
Mar. 14, 2018    (JP) .................. 2018-046168

(51) Int. Cl.
*A61B 3/135*    (2006.01)
*A61B 3/00*    (2006.01)
*A61B 3/14*    (2006.01)

(52) U.S. Cl.
CPC ............ *A61B 3/135* (2013.01); *A61B 3/0008* (2013.01); *A61B 3/14* (2013.01)

(58) Field of Classification Search
CPC ..... A61B 3/0008; A61B 3/0091; A61B 3/135; A61B 3/14
See application file for complete search history.

(56) References Cited

U.S. PATENT DOCUMENTS

2009/0190093 A1    7/2009    Tanassi et al.
2010/0165293 A1    7/2010    Tanassi et al.
(Continued)

FOREIGN PATENT DOCUMENTS

JP    H10-295644 A    11/1998
JP    2000-116732 A    4/2000
(Continued)

OTHER PUBLICATIONS

International Search Report and Written Opinion mailed on May 7, 2019 for PCT/JP2019/010136 filed on Mar. 13, 2019, 6 pages including English Translation of the International Search Report.
(Continued)

*Primary Examiner* — Jack Dinh
(74) *Attorney, Agent, or Firm* — XSENSUS LLP

(57) ABSTRACT

A slit lamp microscope of an aspect example includes an illumination system, first photographing system, fixation system, movement mechanism, and controller. The illumination system projects slit light onto an anterior segment of a subject's eye from a first direction. The first photographing system photographs the anterior segment onto which the slit light is being projected, from a second direction different from the first direction. The fixation system outputs fixation light for fixation of the subject's eye. The movement mechanism moves the illumination system and the first photographing system. the controller performs a first control for the movement mechanism to move at least the illumination system and a second control for the first photographing system to photograph the anterior segment a plurality of
(Continued)

times in parallel with each other while causing the fixation system to output the fixation light.

8 Claims, 16 Drawing Sheets

(56) References Cited

U.S. PATENT DOCUMENTS

| | | |
|---|---|---|
| 2013/0229625 A1 | 9/2013 | Wei et al. |
| 2015/0085252 A1 | 3/2015 | Fujimura et al. |
| 2016/0345822 A1 | 12/2016 | Fujimura et al. |
| 2018/0144827 A1 | 5/2018 | Tsukada |
| 2021/0366612 A1 | 11/2021 | Tsukada |

FOREIGN PATENT DOCUMENTS

| | | |
|---|---|---|
| JP | 2004-329872 A | 11/2004 |
| JP | 2008-284273 A | 11/2008 |
| JP | 2011-507572 A | 3/2011 |
| JP | 2013-248376 A | 12/2013 |
| JP | 2016-159073 A | 9/2016 |
| JP | 2016-174758 A | 10/2016 |
| JP | 2016-174759 A | 10/2016 |
| JP | 2016-179004 A | 10/2016 |
| JP | 2016-209453 A | 12/2016 |
| JP | 2017-176628 A | 10/2017 |
| JP | 2017-185367 A | 10/2017 |
| WO | 2016/185737 A1 | 11/2016 |

OTHER PUBLICATIONS

Japanese Office Action issued Mar. 22, 2022, in corresponding Japanese Patent Application 2018-046168, 6 pp.
Office Action issued on Feb. 14, 2023, in corresponding Chinese patent Application No. 201980017526.1, 22 pages.
Office Action issued on Mar. 14, 2023, in corresponding Japanese patent Application No. 2022-084243, 7 pages.

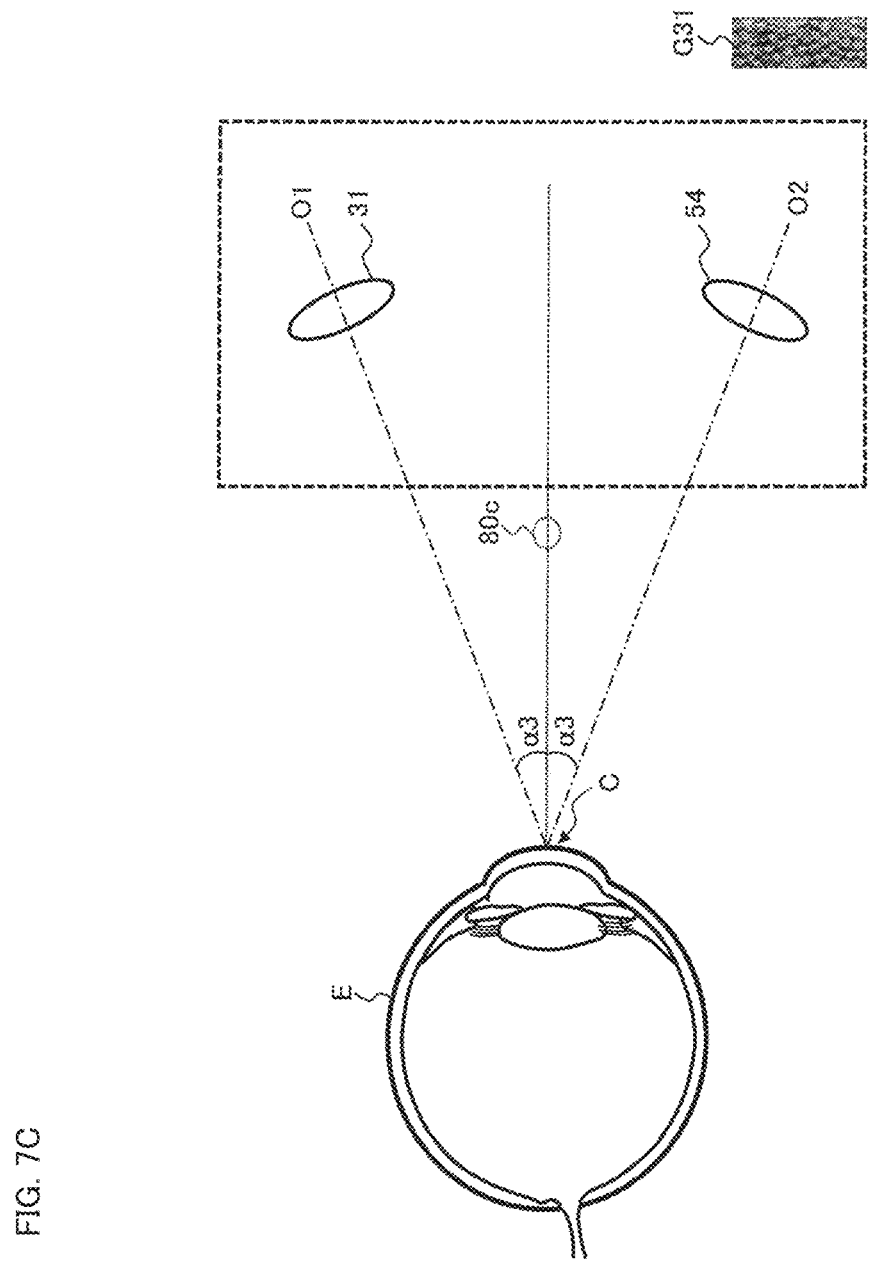

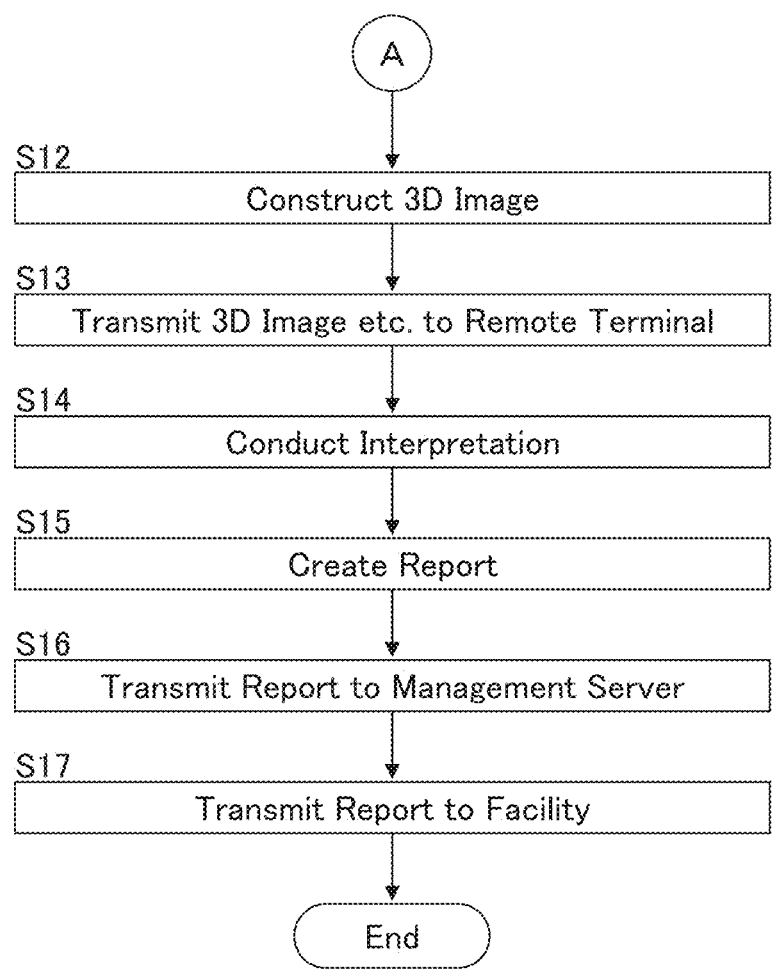

SLIT-LAMP MICROSCOPE AND OPHTHALMIC SYSTEM

CROSS-REFERENCE TO RELATED APPLICATIONS

This application is a national stage (under 35 U.S.C. 371) of International Patent Application No. PCT/JP2019/010136, filed Mar. 13, 2019, claiming priority to Japanese Patent Application No. 2018-046168, filed Mar. 14, 2018, both of which are herein incorporated by reference in their entirety.

FIELD

The present invention relates to a slit lamp microscope and an ophthalmic system.

ART

Diagnostic imaging serves an important role in the field of ophthalmology. Diagnostic imaging uses various kinds of ophthalmic imaging apparatuses. Examples of ophthalmic imaging apparatuses include a slit lamp microscope, a fundus camera, a scanning laser ophthalmoscope (SLO), an optical coherence tomography (OCT) apparatus, and the like. In addition, various kinds of ophthalmic imaging apparatuses, such as a refractometer, a keratometer, a tonometer, a specular microscope, a wave front analyzer, and a micro perimeter, are equipped with the function of imaging anterior eye segment, eye fundus, etc.

A slit lamp microscope is one of the most widely and frequently used apparatuses among various kinds of ophthalmic apparatuses. A slit lamp microscope is an ophthalmic apparatus for illuminating a subject's eye with slit light and observing and/or photographing the illuminated cross section from an oblique position with a microscope. A slit lamp microscope is utilized in general for diagnosis of anterior segments such as corneas or crystalline lenses. For example, a doctor observes an entire diagnostic site while moving the focal position and the area illuminated by the slit light to determine the presence or absence of abnormality. Further, a slit lamp microscope may also be used for prescription of vision correction devices such as for checking of fitting states of contact lenses.

Incidentally, research and development related to telemedicine technology is showing progress with recent advances in information and communication technology. Telemedicine is the act of using information technology such as the Internet to provide medical care (diagnosis, treatment) to a patient in a remote place. Patent Documents 3 and 4 disclose techniques for operating a medical device from a remote location. In particular, Patent Document 4 discloses a technique for operating a slit lamp microscope from a remote location.

[PATENT DOCUMENT 1] Japanese Unexamined Patent Application Publication No. 2016-159073
[PATENT DOCUMENT 2] Japanese Unexamined Patent Application Publication No. 2016-179004
[PATENT DOCUMENT 3] Japanese Unexamined Patent Application Publication No. 2000-116732
[PATENT DOCUMENT 4] Japanese Unexamined Patent Application Publication No. 2008-284273

SUMMARY

An object of the present invention is to provide an ophthalmic telemedicine technology capable of effectively using a slit lamp microscope.

The first aspect of embodiment examples is a slit lamp microscope including an illumination system, a first photographing system, a fixation system, a movement mechanism, and a controller. The illumination system is configured to project slit light onto an anterior segment of a subject's eye from a first direction. The first photographing system is configured to photograph the anterior segment onto which the slit light is being projected, from a second direction different from the first direction. The fixation system is configured to output fixation light for fixation of the subject's eye. The movement mechanism is configured to be capable of moving the illumination system and the first photographing system. The controller is configured to perform a first control for the movement mechanism to move at least the illumination system and a second control for the first photographing system to photograph the anterior segment a plurality of times in parallel with each other while causing the fixation system to output the fixation light.

The second aspect of embodiment examples is the slit lamp microscope of the first aspect, wherein the controller is configured to perform the first control to move the illumination system and the first photographing system together with each other.

The third aspect of embodiment examples is the slit lamp microscope of the first or second aspect, further including a second photographing system. The second photographing system is configured to photograph the anterior segment. Further, the controller is configured to perform a third control for the second photographing system to photograph the anterior segment a plurality of times in parallel with the first control and the second control.

The fourth aspect of embodiment examples is the slit lamp microscope of any of the first to third aspects, wherein the movement mechanism is configured to be capable of moving the illumination system and the first photographing system independently of each other.

The fifth aspect of embodiment examples is the slit lamp microscope of any of the first to fourth aspects, further including a memory. The memory stores initial position information in advance. The initial position information records an initial position of the illumination system and an initial position of the first photographing system. Further, the controller is configured to control the movement mechanism based on the initial position information to place the illumination system and the first photographing system at respective initial positions.

The sixth aspect of embodiment examples is the slit lamp microscope of any of the first to fifth aspects, wherein the movement mechanism is configured to be capable of changing at least a movement direction of the illumination system under the first control.

The seventh aspect of embodiment examples is the slit lamp microscope of the sixth aspect, further including an orientation changing unit. The orientation changing unit is configured to change an orientation of the slit light projected by the illumination system. Further, at least the movement direction of the illumination system under the first control is a width direction of a cross section of the slit light.

The eighth aspect of embodiment examples is the slit lamp microscope of any of the first to seventh aspects, further including a three dimensional image construction unit. The three dimensional image construction unit is configured to construct a three dimensional image based on a plurality of images acquired by the first photographing system under the second control.

The ninth aspect of embodiment examples is the slit lamp microscope of any of the first to eighth aspects, further including a communication device. The communication device is configured to transmit a plurality of images acquired by the first photographing system under the second control to an information processing apparatus via a communication path.

The tenth aspect of embodiment examples is an ophthalmic system that includes a slit lamp microscope and an information processing apparatus. The slit lamp microscope and the information processing apparatus are connected to one another via a communication path. Further, the slit lamp microscope includes: an illumination system, a photographing system, a fixation system, a movement mechanism, a controller, and a first communication device. The illumination system is configured to project slit light onto an anterior segment of a subject's eye from a first direction. The photographing system is configured to photograph the anterior segment onto which the slit light is being projected, from a second direction different from the first direction. The fixation system is configured to output fixation light for fixation of the subject's eye. The movement mechanism is configured to be capable of moving the illumination system and the photographing system. The controller is configured to perform a first control for the movement mechanism to move at least the illumination system and a second control for the photographing system to photograph the anterior segment a plurality of times in parallel with each other while causing the fixation system to output the fixation light. The first communication device is configured to transmit a plurality of images acquired by the photographing system under the second control to the information processing apparatus via the communication path. The information processing apparatus includes a second communication device and a three dimensional image construction unit. The second communication device is configured to receive the plurality of images transmitted by the first communication device. The three dimensional image construction unit is configured to construct a three dimensional image based on the plurality of images received by the second communication device.

BRIEF DESCRIPTION OF THE DRAWINGS

FIG. 7C is a schematic diagram for describing an example of the operation of the slit lamp microscope according to the embodiment example.

FIG. 10B is a flowchart illustrating an example of the usage mode of the ophthalmic system according to the embodiment example.

DETAILED DESCRIPTION

Figure 1:
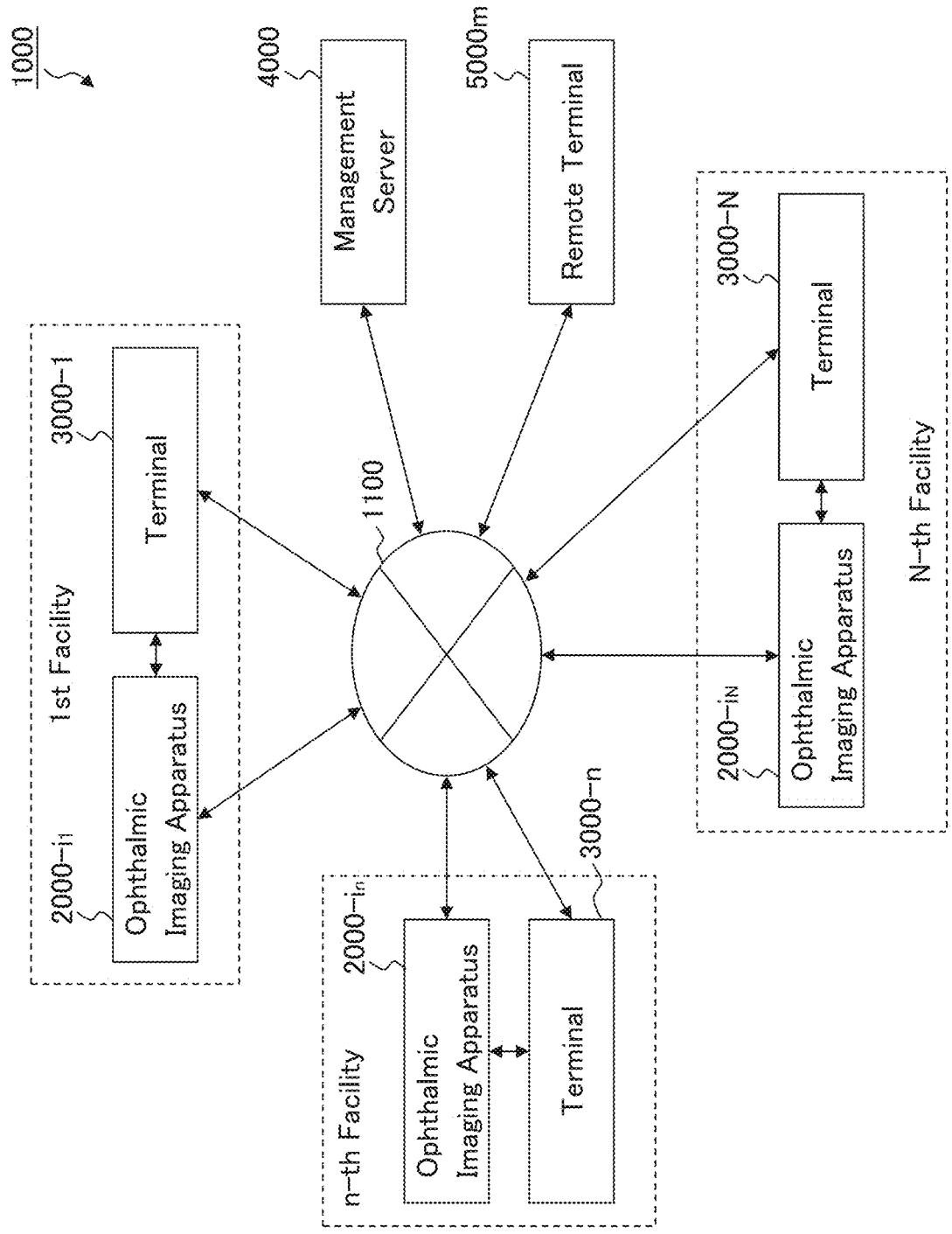
FIG. 1 is a schematic diagram illustrating an example of the configuration of the ophthalmic system according to the embodiment example.

A slit lamp microscope and an ophthalmic system according to embodiment examples will be described in detail with referring to the drawings. It should be noted that any known techniques and technologies such as any of the matters and items disclosed in the documents cited in the present specification may be incorporated into the embodiments.

An ophthalmic system according to some embodiment examples may be utilized for telemedicine using an ophthalmic imaging apparatus installed in any kind of facility and/or a portable ophthalmic imaging apparatus, for example. Telemedicine described in some embodiment examples involves a person who conducts at least interpretation of medical images acquired by an ophthalmic imaging apparatus at a location distant from the facility where the ophthalmic imaging apparatus is installed. The person who conducts the interpretation is typically an expert such as a doctor or an optometrist. The person who conducts the interpretation may create a report on a subject's eye through medical image interpretation. Telemedicine according to some embodiment examples may also involve a person (assistant) who assists examinations at the facility where the ophthalmic imaging apparatus is installed.

Examples of the facility in which the ophthalmic imaging apparatus is installed include an optician's store, a health facility, a health check and screening venue, a patient's home, a welfare facility, a public facility, an examination vehicle, and the like.

The ophthalmic imaging apparatus may be any kind of apparatus used for imaging of eyes and has at least a function of a slit lamp microscope. Any of the plurality of ophthalmic imaging apparatuses included in the ophthalmic system may include an imaging function different from the slit lamp microscope function. For example, the imaging function may be any ophthalmic modalities such as a fundus camera, SLO, or OCT. Furthermore, the ophthalmic imaging apparatus may be provided with application software for analyzing measurement data, captured images, or the like.

The ophthalmic system of the embodiment may further include an ophthalmic measurement apparatus for measuring a characteristic of eyes. Examples of the ophthalmic measurement apparatus include a visual acuity test apparatus (e.g., visual target presenting apparatus, phoropter, etc.), an eye refraction test apparatus (e.g., refractometer, keratometer, etc.), a tonometer, a specular microscope, a wave front analyzer, a perimeter, a micro perimeter, and the like.

<Ophthalmic System>

Some examples of the configuration of the ophthalmic system according to some embodiment example will be described. The ophthalmic system 1000 illustrated in FIG. 1 is configured by using the communication path (communication line) 1100 that connects N facilities (the first to N-th facilities) at which ophthalmic imaging is conducted, the management server 4000, and the remote terminal 5000m.

Each of the facilities (n-th facility: where n=1 to N, N is any positive integer) is provided with the ophthalmic imaging apparatus 2000-$i_n$ (where $i_n$=1 to $K_n$, $K_n$ is any positive integer). In other words, one or more ophthalmic imaging apparatuses 2000-$i_n$ are installed in each of the facilities (n-th facility). The ophthalmic imaging apparatus 2000-$i_n$ constitutes a part of the ophthalmic system 1000. Incidentally, the ophthalmic system 1000 may include an examination apparatus that is capable of performing examination other than ophthalmic examination.

The ophthalmic imaging apparatus 2000-$i_n$ of the present example has the function of an "imaging apparatus" that performs imaging of eyes, and the function of a "computer" that performs various kinds of data processing and communicates with external devices. As described above, the imaging apparatus includes at least a slit lamp microscope. For another example, an imaging apparatus and a computer may be provided separately from each other. If this is the case, the imaging apparatus and the computer may communicate with each other. There may be any number of imaging apparatuses and any number of computers. For example, a single computer and a plurality of imaging apparatuses can be provided.

Each of the facilities (n-th facility) is provided with an information processing apparatus used by an assistant or a subject (i.e., the terminal 3000-n). The terminal 3000-n is a computer for use in the corresponding facility. The terminal 3000-n may be, for example, a mobile terminal such as a tablet terminal or a smartphone, or a server installed in the corresponding facility. The terminal 3000-n may also include a wearable device such as a wireless earphone. Note that the terminal 3000-n is only required to be a computer capable of realizing its functions in the corresponding facility. The terminal 3000-n may be, for example, a computer placed outside the corresponding facility such as a cloud server.

The ophthalmic imaging apparatus 2000-$i_n$ and the terminal 3000-n may communicate with each other through a network such as a network built in the n-th facility (e.g., in-house LAN), a wide area network (e.g., the Internet), or near-field communication technology.

The ophthalmic imaging apparatus 2000-$i_n$ may have the function as a communication device such as a server. If this is the case, the ophthalmic imaging apparatus 2000-$i_n$ and the terminal 3000-n may communicate directly with each other. This makes it possible for the management server 4000 and the terminal 3000-n to communicate with each other via the ophthalmic imaging apparatus 2000-$i_n$. Therefore, the function of performing communication between the terminal 3000-n and the management server 4000 becomes omissible.

The management server 4000 is installed in a facility different from any of the first to N-th facilities, for example, in a management center. The management server 4000 can communicate with the remote terminal 5000m (where m=1 to M, M is any positive integer) via a network. The network is, for example, a LAN or a wide area network. Further, the management server 4000 can communicate with at least one of the ophthalmic imaging apparatuses 2000-$i_n$ installed in the first to N-th facilities via a wide area network.

The management server 4000 has the following functions, for example: the function of relaying communication between the ophthalmic imaging apparatus 2000-$i_n$ and the remote terminal 5000m; the function of recording the contents of the communication; the function of storing data and information acquired by the ophthalmic imaging apparatus 2000-$i_n$; and the function of storing data and information acquired by the remote terminal 5000m. In addition, the management server 4000 may have a data processing function. For example, the management server 4000 may include a three dimensional image constructing unit for executing construction of a three dimensional image from a plurality of cross sectional images acquired by the ophthalmic imaging apparatus 2000-$i_n$ (a slit lamp microscope). The three dimensional image constructing unit includes a processor, a computer program, etc.

The remote terminal 5000m includes a computer that can be used for interpretation of images of acquired from a subject's eye by the ophthalmic imaging apparatus 2000-$i_n$ and for creation of a report.

The "processor" as used in the present embodiment is a circuit such as a central processing unit (CPU), a graphics processing unit (GPU), an application specific integrated circuit (ASIC), and a programmable logic device (PLD). Examples of the PLD include a simple programmable logic device (SPLD), a complex programmable logic device (CPLD), and a field programmable gate array (FPGA). For example, the processor loads a program or data stored in a memory circuit or a storage, and executes the program, thereby implementing the functions according to the embodiment.

<Configuration of the Ophthalmic Imaging Apparatus>

A description is given of an example of the configuration of the ophthalmic imaging apparatus 2000-$i_n$. The ophthalmic imaging apparatus 2000-$i_n$ has functions of a slit lamp microscope, as described above. The ophthalmic imaging apparatus 2000-$i_n$ in the present example is a slit lamp microscope unless otherwise mentioned.

Directions in the present disclosure may be defined as follows in the cases where the optical system of a slit lamp microscope is placed in front of the subject's eye (neutral position): the front direction (or, the depth direction or the Z direction) is defined as the direction towards the subject's eye from the lens positioned closest to the subject's eye (objective lens) in the optical system; the back direction (the −Z direction) is defined as the opposite of the front direction; the left-right direction (or, the lateral direction or the ±X direction) is defined as the horizontal direction orthogonal to the Z direction; and the up-down direction (or, the vertical direction or the ±Y direction) is defined as the direction orthogonal to both the Z direction and the X direction. The XYZ coordinate system is defined as, for example, the right-handed system (or the left-handed system).

Further, the observation-photographing system of the slit lamp microscope is rotatable at least in the horizontal direction. Therefore, the $r_1$ direction is defined as the radial direction that is the direction along the optical axis of the observation-photographing system (referred to as an observation-photographing optical axis). The $\theta_1$ direction is defined as the rotation direction. Similarly, since the illumination system of the slit lamp microscope is also rotatable, the $r_2$ direction is defined as the radial direction that is the direction along the optical axis of the illumination system (referred to as an illumination optical axis), and the $\theta_2$ direction is defined as the rotation direction. For example, the positive direction of the radial direction is defined as the direction from the objective lens towards the subject's eye, and the positive direction of the rotation direction is defined as the counterclockwise direction as seen from above. The rotation direction is defined with the Z direction as a reference (that is, the Z direction is defined as a rotation angle of 0 degrees). When the observation-photographing system is placed at the neutral position (that is, when $\theta_1=0$ degrees), the $r_1$ direction coincides with the Z direction. Similarly, when the illumination system is placed at the neutral position (that is, when $\theta_2=0$ degrees), the $r_2$ direction coincides with the Z direction. At least one of the illumination system and the observation-photographing system may be rotatable in the vertical direction. The radial direction and the rotation direction in this case can be similarly defined.

In addition, the slit lamp microscope of the present embodiment may be configured to be capable of translating the observation-photographing system and the illumination system in a three dimensional manner. For example, the observation-photographing system and the illumination system in the present embodiment may be movable together with one another in the ±X direction, the ±Y direction, and the ±Z direction. Further, the observation-photographing system and the illumination system may be movable independently of each other in the ±X direction, the ±Y direction, and the ±Z direction.

Figure 2:
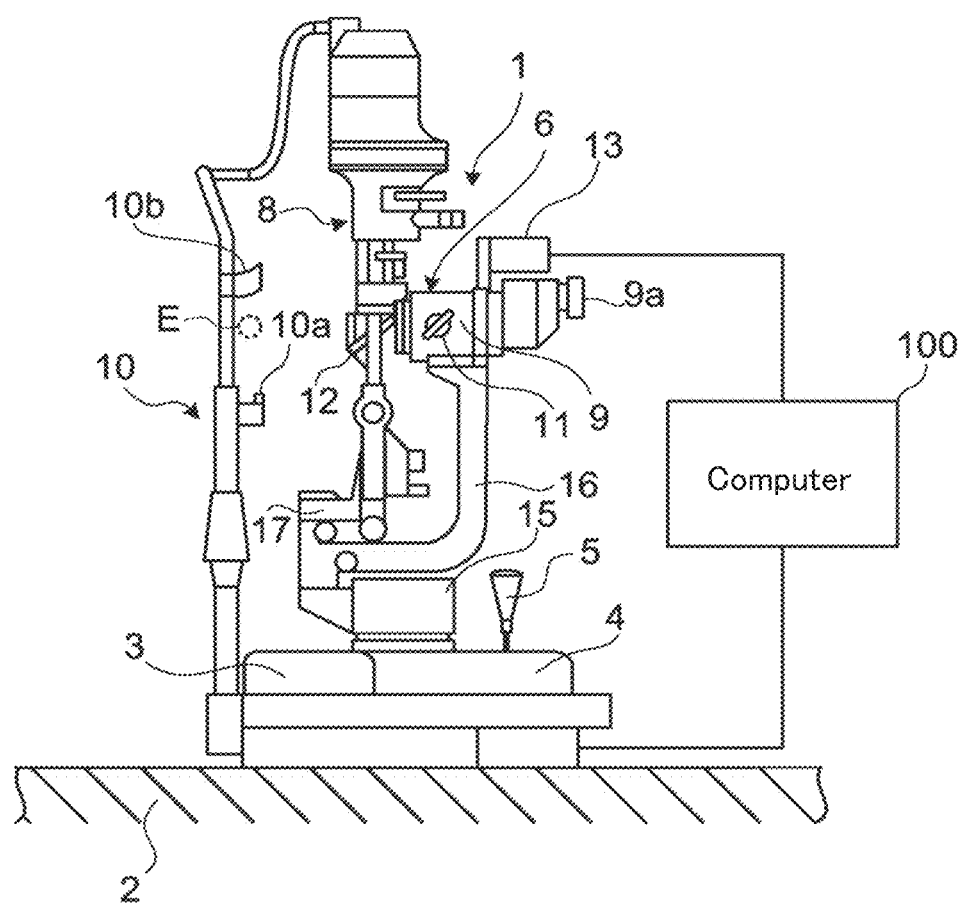
FIG. 2 is a schematic diagram illustrating an example of the configuration of the slit lamp microscope according to the embodiment example.

FIG. 2 shows an example of the exterior configuration of the slit lamp microscope. The computer 100 is connected to the slit lamp microscope 1. The computer 100 executes various kinds of control processing and arithmetic processing. The configuration in which a computer like the computer 100 is provided in the main body of the microscope (housing thereof that stores optical systems etc.) can also be employed in place of providing the computer 100 separately from the main body of the microscope. At least part of the computer 100 and at least part of the aforementioned terminal 3000-$n$ may be common.

The slit lamp microscope 1 is placed on the table 2. The base 4 is configured to be movable in a three dimensional manner via the movement mechanism part 3, for example. More specifically, the movement mechanism part 3 is capable of translating the base 4 in the ±X direction, the ±Y direction, and the ±Z direction. The base 4 is moved by tilting the operation handle 5. Alternatively, the movement mechanism part 3 includes an actuator that is electrically controllable.

The support portion 15 is provided on the upper surface of the base 4. The support portion 15 is configured to support the observation-photographing system 6 and the illumination system 8. The support arm 16 that supports the observation-photographing system 6 is attached to the support portion 15. The support arm 16 is rotatable (i.e., moving in a circular path) in the lateral direction. The support arm 17 that supports the illumination system 8 is attached to the upper portion of the support arm 16. The support arm 17 is rotatable in the lateral direction. The support arms 16 and 17 are independently rotatable in a coaxial manner with each other.

The observation-photographing system 6 is moved by the rotation of the support arm 16. The illumination system 8 is moved by the rotation of the support arm 17. Each of the support arms 16 and 17 is rotated by an electrical mechanism. The movement mechanism part 3 is provided with a mechanism for rotating the support arm 16 and a mechanism for rotating the support arm 17. The movement of the observation-photographing system 6 may be performed by manual rotation of the support arm 16. Likewise, the movement of the illumination system 8 may be performed by manual rotation of the support arm 17.

The illumination system 8 illuminates the subject's eye E with illumination light. As described above, the illumination system 8 can be rotated in the lateral direction. Further, the illumination system 8 may be rotatable in the vertical direction. In other words, the elevation angle and the depression angle of the illumination system 8 may be changeable. By such swinging motions of the illumination system 8, the projection direction of the illumination light with respect to the subject's eye E can be changed.

The observation-photographing system 6 and the illumination system 8 are translated in the ±X direction, the ±Y direction, and the ±Z direction by the movement mechanism part 3. The movement mechanism part 3 may be capable of translating the observation-photographing system 6 and the illumination system 8 together with one another. Further, the movement mechanism part 3 may be capable of translating only the observation-photographing system 6 and translating only the illumination system 8. In other words, the movement mechanism part 3 may be capable of translating the observation-photographing system 6 and the illumination system 8 independently of each other.

Similarly, the observation-photographing system 6 and the illumination system 8 are rotated in the lateral direction and the vertical direction by the movement mechanism part 3. The movement mechanism part 3 may be capable of rotating the observation-photographing system 6 and the illumination system 8 together with one another. Further, the movement mechanism part 3 may be capable of rotating only the observation-photographing system 6 and rotating only the illumination system 8. In other words, the movement mechanism part 3 may be capable of rotating the observation-photographing system 6 and the illumination system 8 independently of each other.

The observation-photographing system 6 includes a pair of left and right optical systems. Each of the left and right optical systems is configured to guide returning light of the illumination light projected onto the subject's eye E. The left and right optical systems are stored in the body tube (or, lens tube, lens barrel, etc.) 9. The terminal end of the body tube 9 is the eyepiece portion 9a. The examiner can conduct observation of the subject's eye E by looking into the eyepiece portion 9a. As described above, the body tube 9 can be rotated in the lateral direction by the rotation of the support arm 16. Further, the observation-photographing system 6 may be configured to be rotatable in the vertical direction. In other words, the elevation angle and the depression angle of the observation-photographing system 6 may be changeable. By such swinging motions of the observation-photographing system 6, the direction of photographing the subject's eye E can be changed.

The chin rest base 10 is disposed at a position facing the body tube 9. The chin rest base 10 is provided with the chin rest 10a and the forehead rest 10b for stably positioning the face of the subject.

The magnification operation knob 11 is disposed on the side surface of the body tube 9. The magnification operation knob 11 is operated to change the magnification. Furthermore, the imaging device 13 that captures an image of the subject's eye E is connected to the body tube 9. The imaging device 13 includes an image sensor. The image sensor is a photoelectric conversion element that detects light and outputs an image signal (an electric signal). The image signal is input to the computer 100. The image sensor may be a charge-coupled device (CCD) image sensor or a complementary metal oxide semiconductor (CMOS) image sensor.

The mirror 12 is disposed at the lower position of the illumination system 8. The mirror 12 reflects and redirects the illumination light beam output from the illumination system 8 toward the subject's eye E.

Although not shown in FIG. 2, the anterior segment camera 70 is provided in the vicinity of the mirror 12. For example, the anterior segment camera 70 is placed at a lower position or an upper position from the mirror 12. The anterior segment camera 70 is used for taking a photograph of the anterior segment of the subject's eye E from the front (or from an oblique direction) (See FIG. 3A to FIG. 4).

<Configuration of the Optical Systems>

Figure 3A:
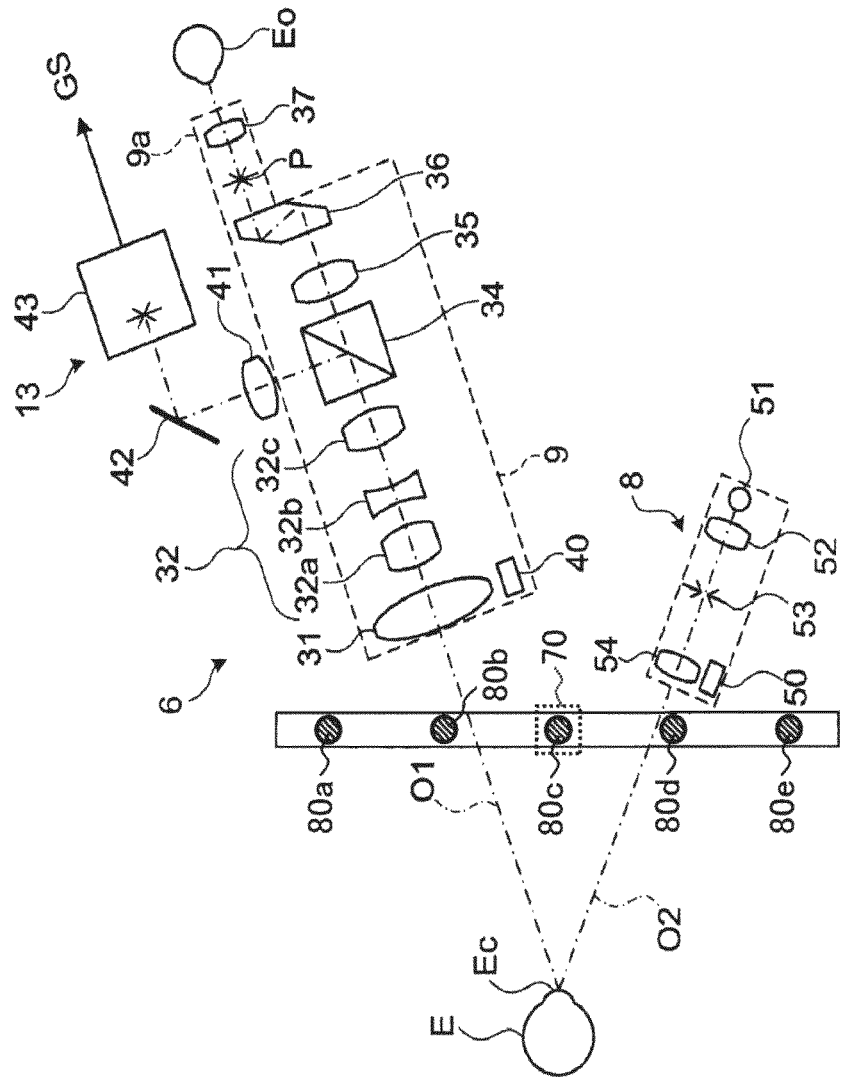
FIG. 3A is a schematic diagram illustrating an example of the configuration of the slit lamp microscope according to the embodiment example.
Figure 3B:
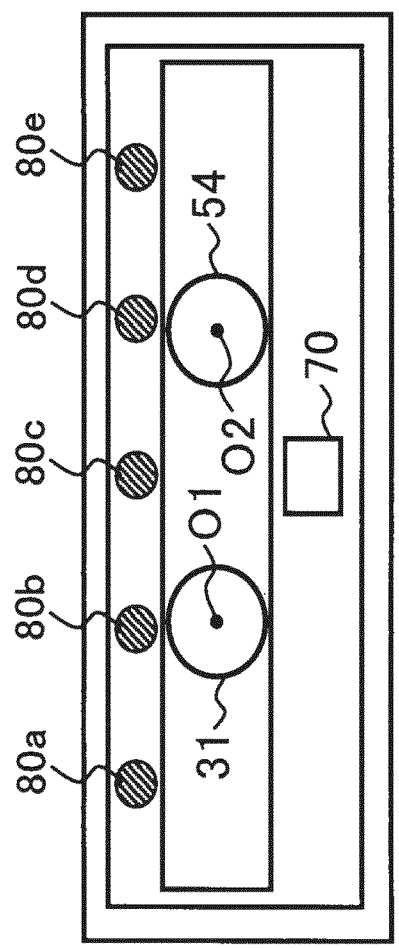
FIG. 3B is a schematic diagram illustrating an example of the configuration of the slit lamp microscope according to the embodiment example.
Figure 3C:
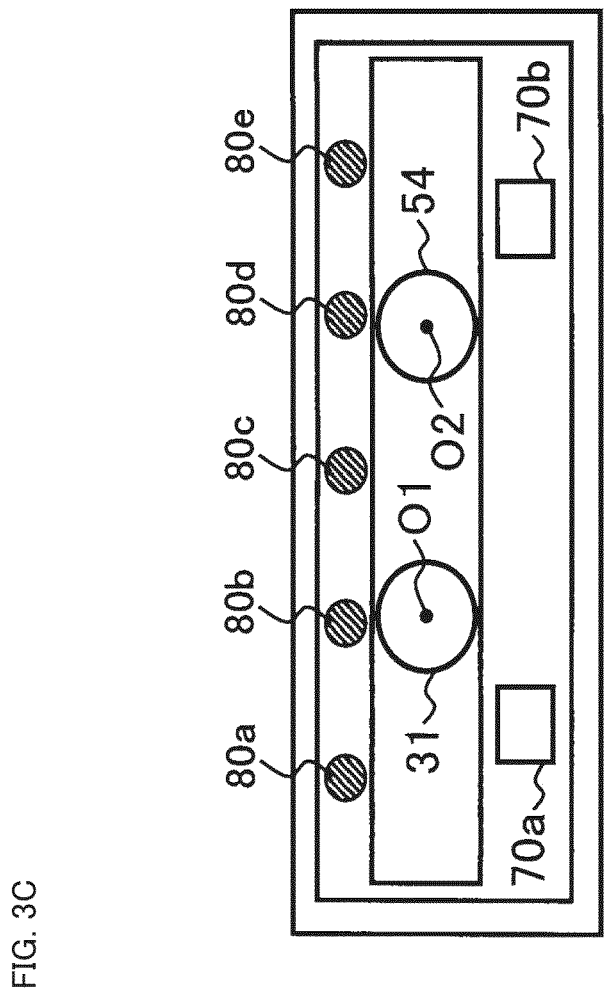
FIG. 3C is a schematic diagram illustrating an example of the configuration of the slit lamp microscope according to the embodiment example.
Figure 4:
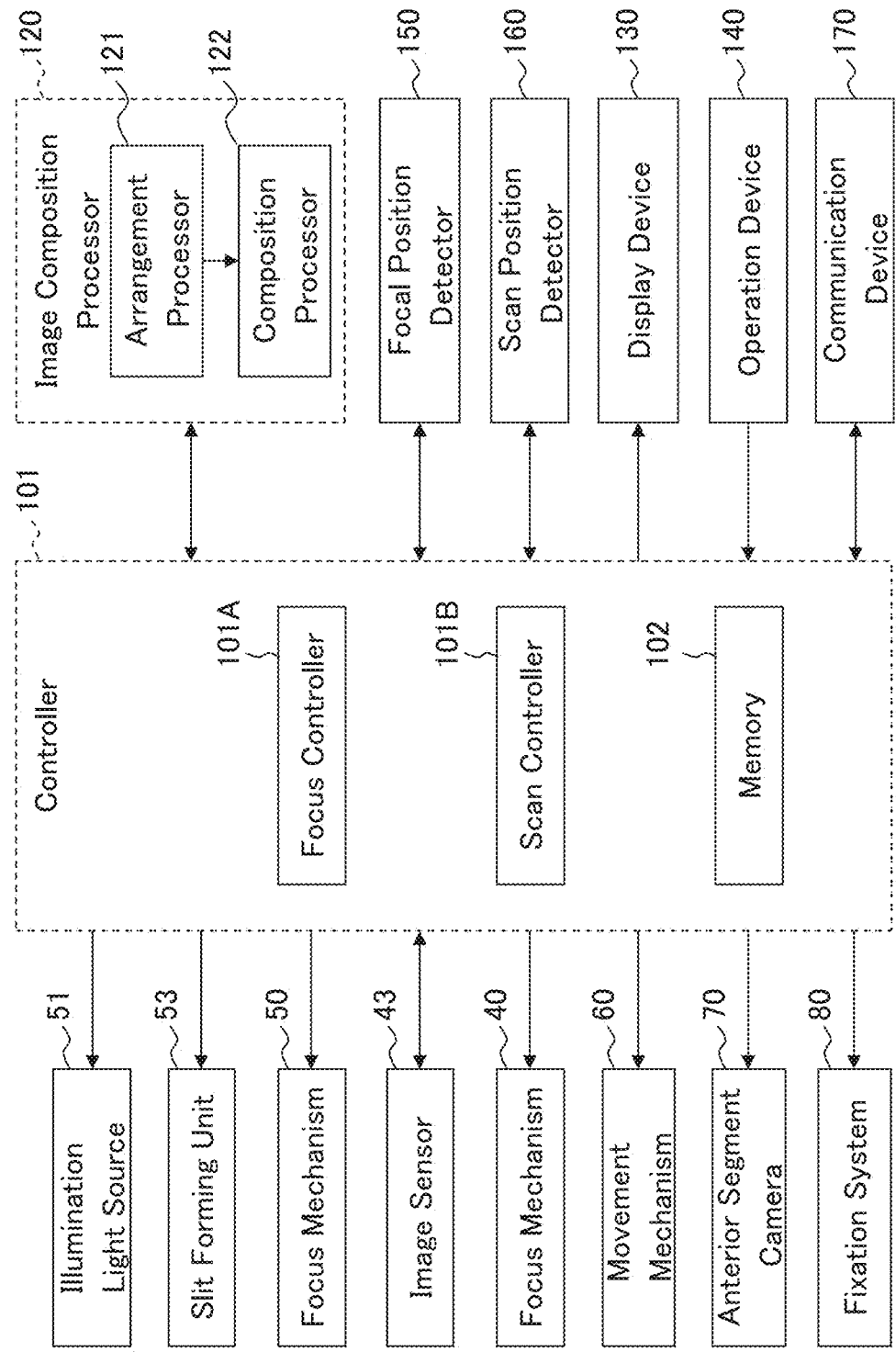
FIG. 4 is a schematic diagram illustrating an example of the configuration of the slit lamp microscope according to the embodiment example.

FIG. 3A and FIG. 3B show an example of the configuration of the optical systems of the slit lamp microscope 1 and FIG. 3C shows another example. FIG. 4 will be referred to as necessary. As described above, the slit lamp microscope 1 includes the observation-photographing system 6 and the illumination system 8.

<Observation-Photographing System 6>

The observation-photographing system 6 includes a pair of left and right optical systems. The left and right optical systems have almost the same configuration. The examiner can observe the subject's eye E with both eyes through the left and right optical systems. FIG. 3A shows only one of the left and right optical systems of the observation-photographing system 6. The observation-photographing system 6 may include only one of the left and right optical systems. The reference character O1 denotes the optical axis of the observation-photographing system 6.

Each of the left and right optical systems of the observation-photographing system 6 includes the objective lens 31, the variable magnification optical system (or zooming optical system) 32, the beam splitter 34, the imaging lens 35, the prism 36, and the eyepiece 37. Here, the beam splitter 34 is provided in one or both of the left and right optical systems. The eyepiece 37 is provided inside the eyepiece portion 9a. The reference character P denotes the imaging position of the light guided to the eyepiece 37. The reference symbol Ec indicates the cornea of the subject's eye E. The reference character Eo denotes the examiner's eye.

The variable magnification optical system 32 includes a plurality of (e.g., three) variable magnification lenses 32a, 32b, and 32c. In the present embodiment, a plurality of variable magnification lens groups is provided. The plurality of variable magnification lens groups is selectively inserted into the optical path of the observation-photographing system 6. The plurality of variable magnification lens groups respectively corresponds to magnifications differing from one another. One of the plurality of variable magnification lens groups selectively disposed in the optical path of the observation-photographing system 6 is used as the variable magnification optical system 32. The selective insertion of the plurality of variable magnification lens groups performed in this way makes it possible to change the magnification (angle of view) of the photographed image and the observation image of the subject's eye E. The change in the magnification, that is, the selection of the variable magnification lens group to be disposed in the optical path of the observation-photographing system 6, is performed by the operation of the magnification operation knob 11. Further, the magnification may be changed by driving the variable magnification optical system 32 with an electrically controllable actuator.

The beam splitter 34 splits the optical path of the light traveling along the optical axis O1 into an optical path located on the extension of the optical axis O1 and an optical path orthogonal to the optical axis O1. The light incident on the optical path located on the extension of the optical axis O1 is guided to the examiner's eye Eo via the imaging lens 35, the prism 36, and the eyepiece 37. The prism 36 translates the traveling direction of the light upward.

On the other hand, the light incident on the optical path orthogonal to the optical axis O1 is guided to the image sensor 43 of the imaging device 13 via the condenser lens 41 and the mirror 42. In other words, the observation-photographing system 6 guides the return light from the subject's eye E to the imaging device 13. The image sensor 43 detects the return light and generates the image signal GS.

The image sensor 43 may be provided in both the left and right optical systems of the observation-photographing system 6. If this is the case, left and right images (moving images or still images) acquired in parallel respectively by the left and right image sensors 43 can be provided to the remote terminal 5000m. Accordingly, the user of the remote terminal 5000m can observe the subject's eye E in a stereoscopic manner.

The observation-photographing system 6 includes the focus mechanism 40 for changing the focal position of the observation-photographing system 6. The focus mechanism 40 moves the objective lens 31 along the optical axis O1. For example, the focus mechanism 40 includes a holding member that holds the objective lens 31, a sliding mechanism that moves the holding member in the direction along the optical axis O1, an actuator that generates driving force, a member that transmits the driving force to the sliding mechanism.

The movement of the objective lens 31 is carried out automatically and/or manually. In the case where automatic movement of the objective lens 31 is employed, for example, the computer 100 can determine the focal position based on the return light from the subject's eye E using a known focus adjustment method (e.g., a phase difference detection method, or a contrast detection method). Further, the computer 100 can control the actuator to move the objective lens 31 along the optical axis O1 to the focal position determined. On the other hand, in the case where manual movement of the objective lens 31 is employed, the actuator moves the objective lens 31 along the optical axis O1 according to an operation performed by the user. This operation is carried out by the user of the slit lamp microscope 1, the user of the terminal 3000-n, or the user of the remote terminal 5000m, for example.

The observation-photographing system 6 may include a first focusing lens that is disposed at a position on the optical axis O1 between the objective lens 31 and the image sensor 43. When the first focusing lens is included, the focus mechanism 40 changes the focal position of the observation-photographing system 6 by moving the first focusing lens along the optical axis O1. For example, the focus mechanism 40 includes a holding member that holds the first focusing lens, a sliding mechanism that moves the holding member in the direction along the optical axis O1, an actuator that generates a driving force, and a member that transmits the driving force to the sliding mechanism. As in the case where the objective lens 31 is moved, the movement of the first focusing lens with the focus mechanism 40 is carried out automatically or manually.

The entire observation-photographing system 6 (or, part of the observation-photographing system 6) may be configured to be movable along the optical axis O1. If this is the case, the focus mechanism 40 changes the focal position of the observation-photographing system 6 by moving the entire (or, part of the) observation-photographing system 6 along the optical axis O1. For example, the focus mechanism 40 includes a movable stage on which the entire (or, part of the) observation-photographing system 6 is placed, a sliding mechanism that moves the movable stage in the direction along the optical axis O1, an actuator that generates a driving force, and a member that transmits the driving force to the sliding mechanism. As in the case where the objective lens 31 is moved, the movement of the observation-photographing system 6 with the focus mechanism 40 is carried out automatically or manually.

<Illumination System 8>

The illumination system 8 includes the illumination light source 51, the condenser lens 52, the slit forming unit 53, and the objective lens 54. The reference character O2 denotes the optical axis of the illumination system 8.

The illumination light source 51 outputs illumination light. The illumination system 8 may include a plurality of light sources. For example, the illumination light source 51 may include both a light source that outputs steady light or continuous light and a light source that outputs flash light. Examples of the light source that outputs steady light or continuous light include a halogen lamp and a light emitting diode (LED). Examples of the light source that outputs flash light include a xenon lamp and an LED. The illumination light source 51 may include a light source for the observation of anterior segment and another light source for the observation of posterior eye segment. For example, the illumination light source 51 includes a visible light source that outputs visible light. The illumination light source 51 may also include an infrared light source that outputs infrared light. The center wavelength of the infrared light is, for example, a value between 800 nm and 1000 nm.

The slit forming unit 53 is used to generate slit light. The slit forming unit 53 has a pair of slit blades. The width of the slit light to be generated can be changed by changing the interval between the slit blades. The interval between the slit blades are referred to as slit width.

The illumination system 8 includes the focus mechanism 50 for changing the focal position of the slit light. The focus mechanism 50 moves the objective lens 54 along the optical axis O2. For example, the focus mechanism 50 includes a holding member that holds the objective lens 54, a sliding mechanism that moves the holding member in the direction along the optical axis O1, an actuator that generates a driving force, and a member that transmits the driving force to the sliding mechanism.

The movement of the objective lens 54 is carried out automatically and/or manually. In the case where the automatic movement of the objective lens 54 is employed, for example, the computer 100 can determine the focal position by analyzing an image that depicts the image corresponding to the return light from the subject's eye E. Further, the computer 100 can control the actuator to move the objective lens 54 along the optical axis O2 to the focal position determined. On the other hand, in the case where manual movement of the objective lens 54 is employed, the actuator moves the objective lens 54 along the optical axis O2 according to an operation performed by the user. This operation is carried out by the user of the slit lamp microscope 1, the user of the terminal 3000-$n$, or the user of the remote terminal 5000$m$, for example.

The illumination system 8 may include a second focusing lens that is disposed at a position on the optical axis O2 between the objective lens 54 and the slit forming unit 53. When the second focusing lens is included, the focus mechanism 50 changes the focal position of the slit light by moving the second focusing lens along the optical axis O2. For example, the focus mechanism 50 includes a holding member that holds the second focusing lens, a sliding mechanism that moves the holding member in the direction along the optical axis O2, an actuator that generates a driving force, and a member that transmits the driving force to the sliding mechanism. As in the case where the objective lens 54 is moved, the movement of the second focusing lens with the focus mechanism 50 is carried out automatically or manually.

The entire illumination system 8 (or, part of the illumination system 8) may be movable along the optical axis O2. If this is the case, the focus mechanism 50 changes the focal position of the slit light by moving the entire (or, part of the) illumination system 8 along the optical axis O2. For example, the focus mechanism 50 includes a movable stage on which the entire (or, part of the) illumination system 8 is placed, a sliding mechanism that moves the movable stage in the direction along the optical axis O2, an actuator that generates a driving force, and a member that transmits the driving force to the sliding mechanism. As in the case where the objective lens 54 is moved, the movement of the illumination system 8 with the focus mechanism 50 is carried out automatically or manually.

Although not shown in the drawing in FIG. 3A to FIG. 3C, the mirror 12 is disposed in the optical axis O2. The mirror 12 reflects and redirects the illumination light beam output from the illumination system 8 toward the subject's eye E. Typically, the illumination system 8 and the mirror 12 are capable of moving (translation, rotating) together with one another.

The slit lamp microscope 1 can acquire a plurality of images by photographing the subject's eye E multiple times in parallel with changing the positions of the illumination system 8 and the observation-photographing system 6 with respect to the subject's eye E. In other words, the slit lamp microscope 1 can acquire a plurality of cross sectional images of the anterior segment by photographing the subject's eye E multiple times in parallel with moving the illumination system 8 and the observation-photographing system 6. The movement of the illumination system 8 and the observation-photographing system 6 for photographing the subject's eye E multiple times may be rotation or translation.

To each of the plurality of cross sectional images acquired through such control, position information indicating a corresponding acquisition position (i.e., corresponding cross sectional position) is assigned. For example, the position information may include any one or more of the followings: a position of the illumination system 8 (e.g., rotational position, translational position); a position of the observation-photographing system 6 (e.g., rotational position, translational position); a position of a cross section in a front image of the anterior segment acquired by the anterior segment camera 70; and information created based on any one or more of the above positions.

The position (i.e., position and/or angle) of the illumination system 8 and/or the position (i.e., position and/or angle) of the observation-photographing system 6 can be detected, for example, with a position detector including an encoder or the like. Alternatively, the position (i.e., position and/or angle) of the illumination system 8 and/or the position (i.e., position and/or angle) of the observation-photographing system 6 can be recognized by the computer 100 that controls the mechanism for moving the illumination system 8 and/or the mechanism for moving the observation-photographing system 6. The position of a cross section in a front image of the anterior segment of the subject's eye E can be determined based on, for example, a front image of the anterior segment acquired by the anterior segment camera 70 and position(s) detected by the aforementioned position detector. A three dimensional image of the anterior segment can be constructed from a plurality of cross sectional images and a plurality of pieces of position information respectively assigned to the plurality of cross sectional images. Details of such three dimensional construction will be described later.

It is to be noted that the plurality of times of photography of the subject's eye E carried out in parallel with performing the changes in the position of the illumination system 8 and the position of the observation-photographing system 6 may be carried out while at least one of the illumination system 8 and the observation-photographing system 6 is moving, or while at least one of the illumination system 8 and the observation-photographing system 6 is stationary. The movement of the illumination system 8 may be in a continuous or intermittent manner, and the movement of the observation-photographing system 6 may also be in a continuous or intermittent manner.

The slit lamp microscope 1 can acquire a plurality of images by photographing the subject's eye E multiple times in parallel with performing the change in the focal position with respect to the subject's eye E. More specifically, the slit lamp microscope 1 can acquire a plurality of cross sectional images of the anterior segment of the subject's eye E by photographing the subject's eye E multiple times in parallel with performing at least one of the change in the focal position of the observation-photographing system 6 and the change in the focal position of the illumination system 8.

To each of the plurality of cross sectional images acquired through such control, position information indicating a corresponding acquisition position (e.g., corresponding focal position) is assigned. The position information may include any one or more of the followings: contents of control for the focus mechanism 40; contents of control for the focus mechanism 50; a position of a member to be moved by the focus mechanism 40 such as the objective lens 31, the first focusing lens, or the observation-photographing system 6; a position of a member to be moved by the focus mechanism 50 such as the objective lens 54, the second focusing lens, or the illumination system 8; and information created based on any one or more of the pieces of information (contents of controls, positions) described above.

Control contents for the focus mechanism 40 or 50 can be recognized, for example, by the computer 100 that controls the focus mechanisms 40 or 50. The position of a member to be moved by the focus mechanism 40 or 50 can be detected, for example, by a position detector including an encoder or the like. A three dimensional image of the anterior segment can be constructed from a plurality of cross sectional images and at least one of a plurality of control contents and a plurality of pieces of position information respectively assigned to the plurality of cross sectional images. Details of the three dimensional construction will be described later.

It is to be noted that the plurality of times of photography of the subject's eye E carried out in parallel with performing the change in the focal position may be performed while the focal position is changing, or while the focal position is stationary. The change in the focal position may be in a continuous or intermittent manner.

The two kinds of controls described above may be combined. For example, the slit lamp microscope 1 can acquire a plurality of cross sectional images by photographing the subject's eye E multiple times in parallel with performing the changes in the following positions: the position of the illumination system 8; the position of the observation-photographing system 6; the focal position of the illumination system 8; and the focal position of the observation-photographing system 6. To each of the plurality of cross sectional images acquired through the combined control, position information indicating a corresponding acquisition positions (e.g., cross sectional position and focal position) is assigned.

<Anterior Segment Camera 70>

The anterior segment camera 70 photographs the anterior segment from a front position or an oblique position. FIG. 3A and FIG. 3B show an example in which the anterior segment can be photographed from the front, and FIG. 3C shows an example in which the anterior segment can be photographed from an oblique direction. Note that each or both of the two anterior segment cameras 70a and 70b illustrated in FIG. 3C may be referred to as the anterior segment camera 70.

The anterior segment camera 70 is, for example, a video camera capable of acquiring a moving image. The anterior segment camera 70 is fixedly placed. Alternatively, the anterior segment camera 70 may be moved independently of the movement of the observation-photographing system 6 and the illumination system 8.

The anterior segment camera 70 may be provided in any number of one or more. For example, the single anterior segment camera 70 is provided at the center position in the lateral direction in the example shown in FIG. 3A and FIG. 3B. On the other hand, the two anterior segment cameras 70a and 70b that are spaced apart in the lateral direction are provided in the example shown in FIG. 3C.

In the case that two or more anterior segment cameras are provided as in the example shown in FIG. 3C, the slit lamp microscope can carry out the alignment method disclosed by the present applicant in Japanese Unexamined Patent Application Publication No. 2013-248376. This alignment method includes, for example, the following steps: a step of photographing the anterior segment from different directions by two or more anterior segment cameras to acquire two or more photographed images; a step of analyzing the photographed images by a processor such as the computer 100 to determine a three dimensional position of the subject's eye; and a step of controlling the movement mechanism part 3 by a processor such as the computer 100 based on the three dimensional position determined. With such an alignment operation, the optical system (for example, the observation-photographing system 6 and/or the illumination system 8) is brought to and placed at an appropriate alignment position.

Alignment methods applicable to the exemplary embodiment are not limited to the above-described alignment method. For example, any method applicable to the alignment between the subject's eye and the optical system(s) of the apparatus may be employed, such as an alignment method using a Purkinje image formed by alignment light and an alignment method using an optical lever.

An anterior segment illumination light source may be provided. The anterior segment illumination light source is configured to project illumination light onto the anterior segment for the anterior segment camera 70 to conduct photography. The anterior segment illumination light source may be, for example, an infrared light source or a visible light source. The anterior segment illumination light source is disposed, for example, in the vicinity of the anterior segment camera 70. For example, the anterior segment illumination light source is placed at a lower position, an upper position, or a side position from the anterior segment camera 70. The number of the anterior segment illumination light sources provided in some embodiment examples may be any number of one or more.

<Fixation System 80>

The fixation system 80 outputs fixation light for fixation of the subject's eye E. The fixation system 80 includes a plurality of visible light sources (referred to as fixation light sources). In the examples of FIG. 3A to FIG. 3C, five fixation light sources 80a to 80e are provided. The fixation light sources 80a to 80e are arranged in a line along the lateral direction (X direction). The fixation light sources 80a to 80e are turned on in a selective manner.

The number of fixation light sources provided in the fixation system 80 may be an arbitrary number of one or more. The fixation system 80 of another aspect may include a movable fixation light source. The fixation system 80 of another aspect may include a display device capable of displaying a fixation target at a desired position on the display screen.

<Configuration of Control System>

Figure 5:
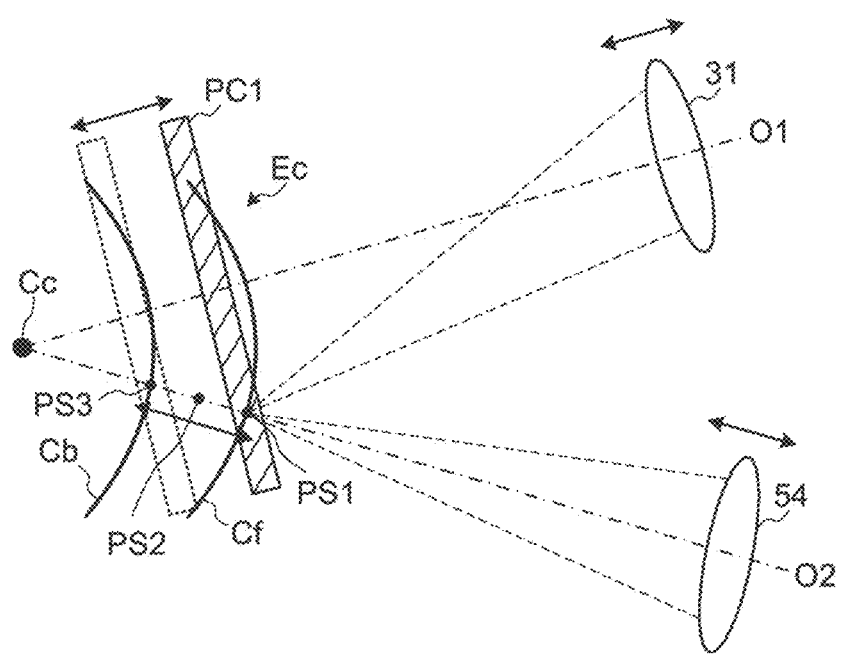
FIG. 5 is a schematic diagram for describing an example of the operation of the slit lamp microscope according to the embodiment example.

The control system of the slit lamp microscope 1 will be described with reference to FIG. 4 to FIG. 6. FIG. 4 shows an example of the configuration of the control system of the slit lamp microscope 1. Note that the computer 100 may include at least part of a plurality of elements constituting the control system.

<Controller 101>

The controller 101 controls each part of the slit lamp microscope 1. The controller 101 controls, for example, the observation-photographing system 6, the illumination system 8, the movement mechanism 60, the anterior segment camera 70, the image composition processor 120, the display device 130, the focal position detector 150, the scan position detector 160, the communication device 170, etc.

The movement mechanism 60 moves the illumination system 8 and the observation-photographing system 6. The movement mechanism 60 includes, for example, the movement mechanism part 3, the support arms 16 and 17, and a mechanism that moves the support arms 16 and 17. The movement mechanism 60 may be capable of moving the illumination system 8 and the observation-photographing system 6 independently of each other. The independent movement includes, for example, at least rotation of the illumination system 8 and rotation of the observation-photographing system 6. Further, the independent movement may include at least one of translation of the illumination system 8 and translation of the observation-photographing system 6. The independent movement makes it possible to change the position of the illumination system 8 with respect to the subject's eye E (illumination position, illumination angle) and to change the position of the observation-photographing system 6 with respect to the subject's eye E (observation position, observation angle, photographing position, photographing angle).

The illumination angle herein may be defined as the angle with respect to the optical axis of the illumination system 8 (the illumination optical axis) in the state that the illumination system 8 is located at a predetermined reference position (neutral position). Similarly, the observation angle and the photographing angle may be defined as the angles with respect to the optical axis of the observation-photographing system 6 (the observation-photographing optical axis) in the state that the observation-photographing system 6 is located at a predetermined reference position (neutral position). The reference of the illumination angle and the reference of the observation angle and the photographing angle may be the same or different from each other. As described above, the observation angle and the photographing angle in the present example are represented by the angle $\theta_1$ formed by the $r_1$ direction with respect to the Z direction, and the illumination angle is represented by the angle $\theta_2$ formed by the $r_2$ direction with respect to the Z direction.

The movement mechanism 60 may be capable of moving the illumination system 8 and the observation-photographing system 6 together with one another. Such combined movement includes, for example, at least one of translation and rotation. The combined translation can be employed, for example, in order to conduct scanning of the anterior segment along with maintenance of both the illumination angle and the photographing angle. The combined rotation can be employed, for example, in order to conduct scanning of the anterior segment while (continuously or stepwise) changing both the illumination angle and the photographing angle.

Controls relating to the observation-photographing system 6 may include any one or more of the followings: control for the variable magnification optical system 32; control for the image sensor 43; control for the focus mechanism 40; control for the movement mechanism 60 that moves the observation-photographing system 6; control for the focal position detector 150; and control for the scan position detector 160. The control for the variable magnification optical system 32 may include control for changing the magnification (magnification ratio) of an observation image or a photographed image of the subject's eye E in accordance with the content of an operation performed using the magnification operation knob 11. Controls for the image sensor 43 may include any of the followings: control for changing electric charge accumulation time, sensitivity, frame rate, etc. of the image sensor 43; and control for sending the image signal GS generated by the image sensor 43 to the image composition processor 120. Controls for the focus mechanism 40 may include control for changing the focal position of the observation-photographing system 6. Control for the movement mechanism 60 may include control for moving (rotating, translating) the observation-photographing system 6. Control for the focal position detector 150 may include control for acquiring the position detected by the focal position detector 150, and control for sending the acquired position to the image composition processor 120. Control for the scan position detector 160 may include control for acquiring the position detected by the scan position detector 160, and control for sending the acquired position to the image composition processor 120.

Controls relating to the illumination system 8 may include the followings: control for the illumination light source 51; control for the slit forming unit 53; control for the focus mechanism 50; control for the movement mechanism 60 for moving the illumination system 8; control for the focal position detector 150; and control for the scan position detector 160. The control for the illumination light source 51 may include control for switching on and off the illumination light source 51, and control for changing the quantity of the illumination light. The control for the slit forming unit 53 may include control for changing the slit width, control for translating the slit, and control for rotating the slit. The control for the focus mechanism 50 may include control for changing the focal position of the slit light (the focal position of the illumination system 8). The control for the movement mechanism 60 may include control for moving (rotating, translating) the illumination system 8. The control for the focal position detector 150 may include control for acquiring the position detected by the focal position detector 150, and control for sending the acquired position to the image composition processor 120. The control for the scan position detector 160 may include control for acquiring the position detected by the scan position detector 160, and control for sending the acquired position to the image composition processor 120.

The controller 101 includes the focus controller 101A, the scan controller 101B, and the memory 102.

The focus controller 101A executes the control for the focal position of the observation-photographing system 6 and the control for the focal position of the illumination system 8.

The controls carried out by the focus controller 101A will be described with reference to FIG. 5. FIG. 5 schematically shows the focal positions of the observation-photographing system 6 and the illumination system 8 with respect to the cornea Ec of the subject's eye E. As described above, the reference character 31 denotes the objective lens of the observation-photographing system 6, and the reference character 54 denotes the objective lens of the illumination system 8. The reference character Cf denotes the front surface of the cornea Ec, and the reference character Cb denotes the back surface of the cornea Ec. The reference character Cc denotes the position of the center of curvature of the cornea Ec (the position of the center of curvature of the front surface Cf). For example, the rotation axis of the observation-photographing system 6 and that of the illumination system 8 both substantially coincide with the curvature center position Cc.

The focus controller 101A controls a scan in the depth direction with respect to the site of interest of the subject's eye E. The depth direction with respect to the site of interest corresponds to the radial direction in the rotational operation. Such a scan is referred to as an r-scan. The focus controller 101A can execute the control of the focus mechanism 40 and the control of the focus mechanism 50 in an interlocking manner. For example, the focus controller 101A controls the focus mechanism 40 and the focus mechanism 50 to change the focal position of the observation-photographing system 6 and the focal position of the illumination system 8 in the order of the positions PS1, PS2 and PS3. The positions PS1, PS2 and PS3 are arranged along the depth direction of the site of interest, that is, along the depth direction in the subject's eye E. The observation-photographing system 6 can perform photography of the subject's eye E with depths of field respectively corresponding to the focal positions applied. For example, the observation-photographing system 6 can capture an image of the subject's eye E in the depth of field PC1 corresponding to the position PS1.

The focus controller 101A can execute the control for the imaging device 13 to capture an image and the interlocking control described above in an alternate manner. With this, the focus controller 101A can control the acquisition of a plurality of cross sectional images arranged in the depth direction of the site of interest of the subject's eye E. For example, the focus controller 101A can perform the control in such a way that an image of a cross section including the position PS1, an image of a cross section including the position PS2, and an image of a cross section including the position PS3 are sequentially captured.

The scan controller 101B performs control to move the scan position with respect to the site of interest of the subject's eye E in the horizontal direction (i.e., in the direction substantially orthogonal to the depth direction). Although detailed description is omitted, control to move the scan position in the vertical direction can also be executed in the same manner. Here, the vertical direction is substantially orthogonal to both the horizontal direction and the depth direction.

The operation of the scan controller 101B will be described with reference to FIG. 6. FIG. 6 schematically shows the focal positions of the observation-photographing system 6 and the illumination system 8 with respect to the cornea Ec. In FIG. 6, parts, sites, elements, etc. that are the same as or similar to those in FIG. 5 are indicated by the same reference characters, and descriptions thereof are omitted unless otherwise stated.

The scan controller 101B controls a scan in the horizontal direction with respect to the site of interest of the subject's eye E. The horizontal direction with respect to the site of interest corresponds to the angle direction in the rotational operation. Such a scan is referred to as a θ-scan. The scan controller 101B can execute the control of the movement mechanism 60 so as to interlock the rotation of the illumination system 8 and the rotation of the observation-photographing system 6 with each other. For example, the scan controller 101B moves the observation-photographing system 6 and the illumination system 8 in the order of the scan positions PS1, PS11, and PS12 in the horizontal direction.

The scan controller 101B can execute the control for the imaging device 13 to capture an image and the control for the movement mechanism 60 in an alternate manner. With this, the scan controller 101B can control the acquisition of a plurality of cross sectional images arranged in the horizontal direction in the site of interest of the subject's eye E. For example, the scan controller 101B can perform control in such a way that an image of a cross section including the position PS1, an image of a cross section including the position PS11, and an image of a cross section including the position PS12 are sequentially captured.

At each of the positions PS1, PS11, and PS12 in the horizontal direction, the focus controller 101A can change the focal position of the observation-photographing system 6 and the focal position of the illumination system 8 in the depth direction. As a result of this, one or more cross sectional images can be acquired for each of the positions PS1, PS2, PS3, PS11, PS21, PS31, PS12, PS22, and PS32.

Figure 6:
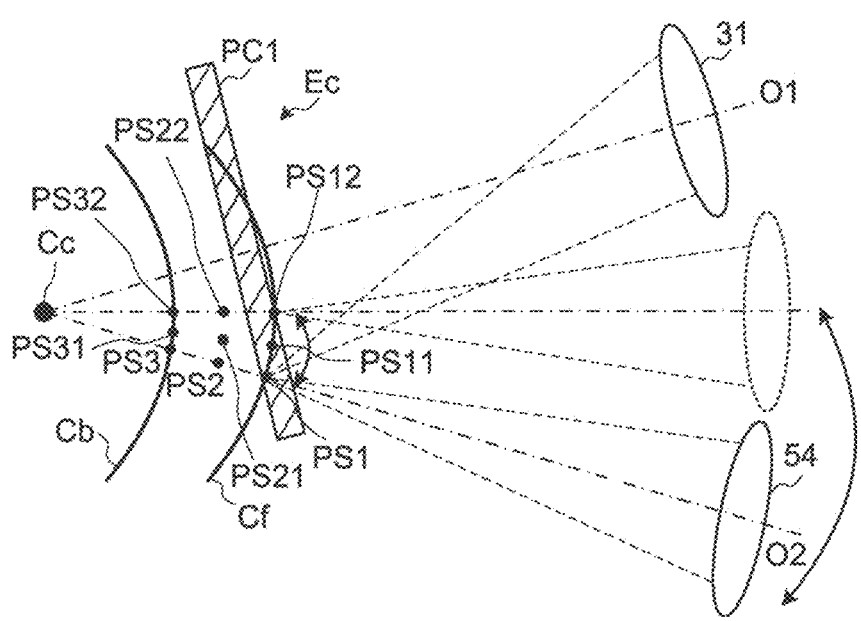
FIG. 6 is a schematic diagram for describing an example of the operation of the slit lamp microscope according to the embodiment example.

While FIG. 6 describes scanning by means of rotation of the optical system, scanning may be performed by means of translation of the optical system.

Figure 7A:
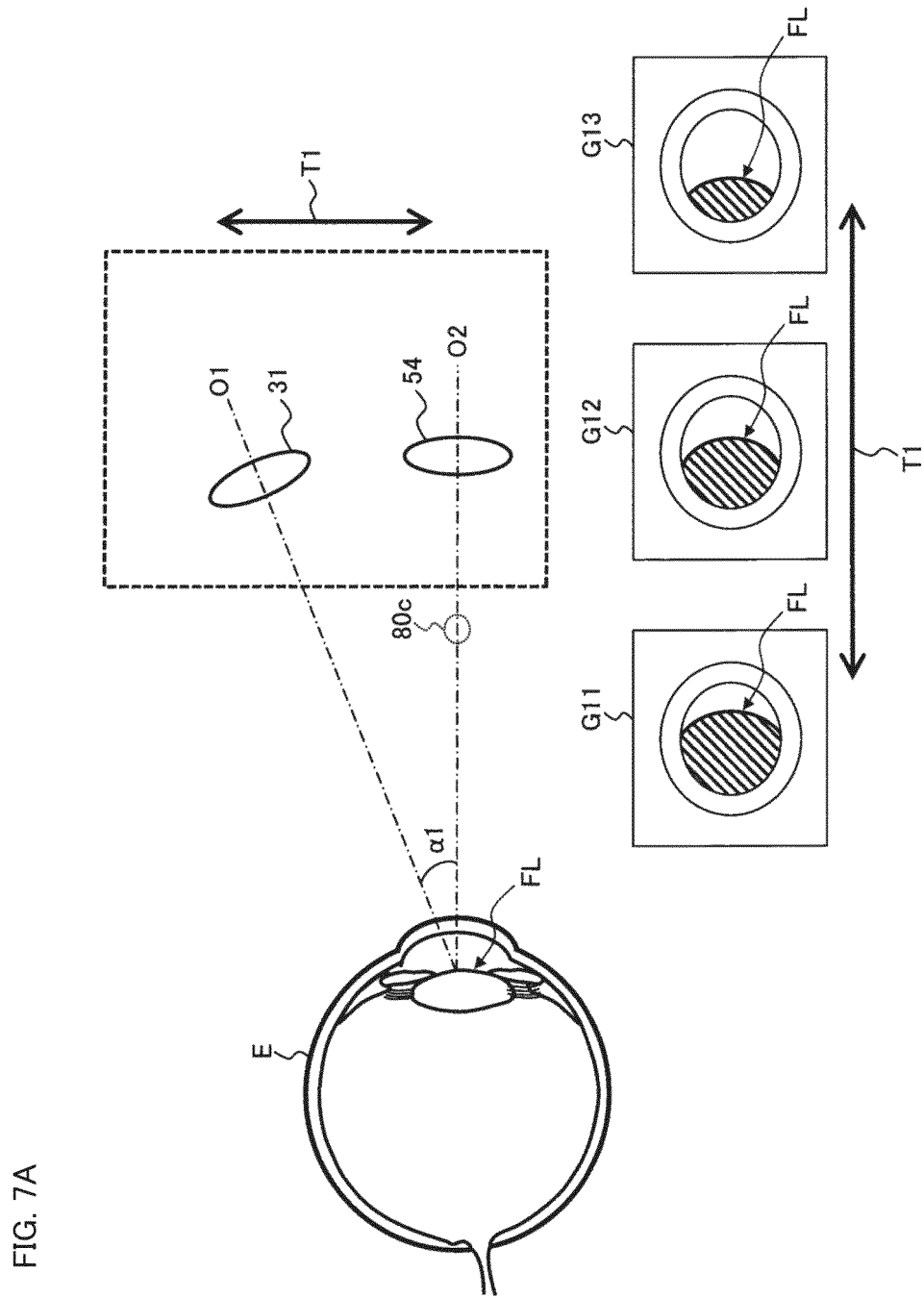
FIG. 7A is a schematic diagram for describing an example of the operation of the slit lamp microscope according to the embodiment example.

For example, in the case of conducting photography by focusing on the anterior capsule FL of the crystalline lens as shown in FIG. 7A, the observation-photographing system 6 may be placed at a position where the photographing angle $\theta_1=0$ degrees (neutral position), and the illumination system 8 may be placed at a position where the illumination angle $\theta_2=\alpha 1 \neq 0$ degrees.

In such an arrangement state of the optical systems, the scan controller 101B controls the movement mechanism 60 to translate the observation-photographing system 6 and the illumination system 8 together with one another in the +X direction and/or the −X direction (the translation indicated by the arrow T1). In the present example, the fixation light source 80c that substantially coincides with the neutral position is turned on. The fixation position does not change even when the observation-photographing system 6 and the illumination system 8 are translated. This means that the fixation position does not move during the translation scan of the present example.

In parallel with such control of the movement mechanism 60, the scan controller 101B executes control of the observation-photographing system 6 to perform photography a plurality of times. As an example of this photography control, the scan controller 101B may repeatedly send an imaging trigger signal to the observation-photographing system 6 in parallel with executing the control of the movement mechanism 60. Alternatively, the scan controller 101B may send a control signal for starting moving image acquisition to the observation-photographing system 6 before or at the same time as executing the control of the movement mechanism 60.

With such controls, photography may be conducted a plurality of times while relatively moving the observation-photographing system 6 and the illumination system 8 with respect to the subject's eye E. The images G11, G12, and G13 illustrated in FIG. 7A schematically show some of a plurality of images acquired by the control of the present example. The depiction position of the anterior capsule FL changes corresponding to the translation indicated by the arrow T1, as shown in the images G11 to G13. In this way, a plurality of images corresponding to a plurality of cross sections (a plurality of cross sections arranged in the X direction) of the crystalline lens (the anterior capsule FL) are acquired.

Figure 7B:
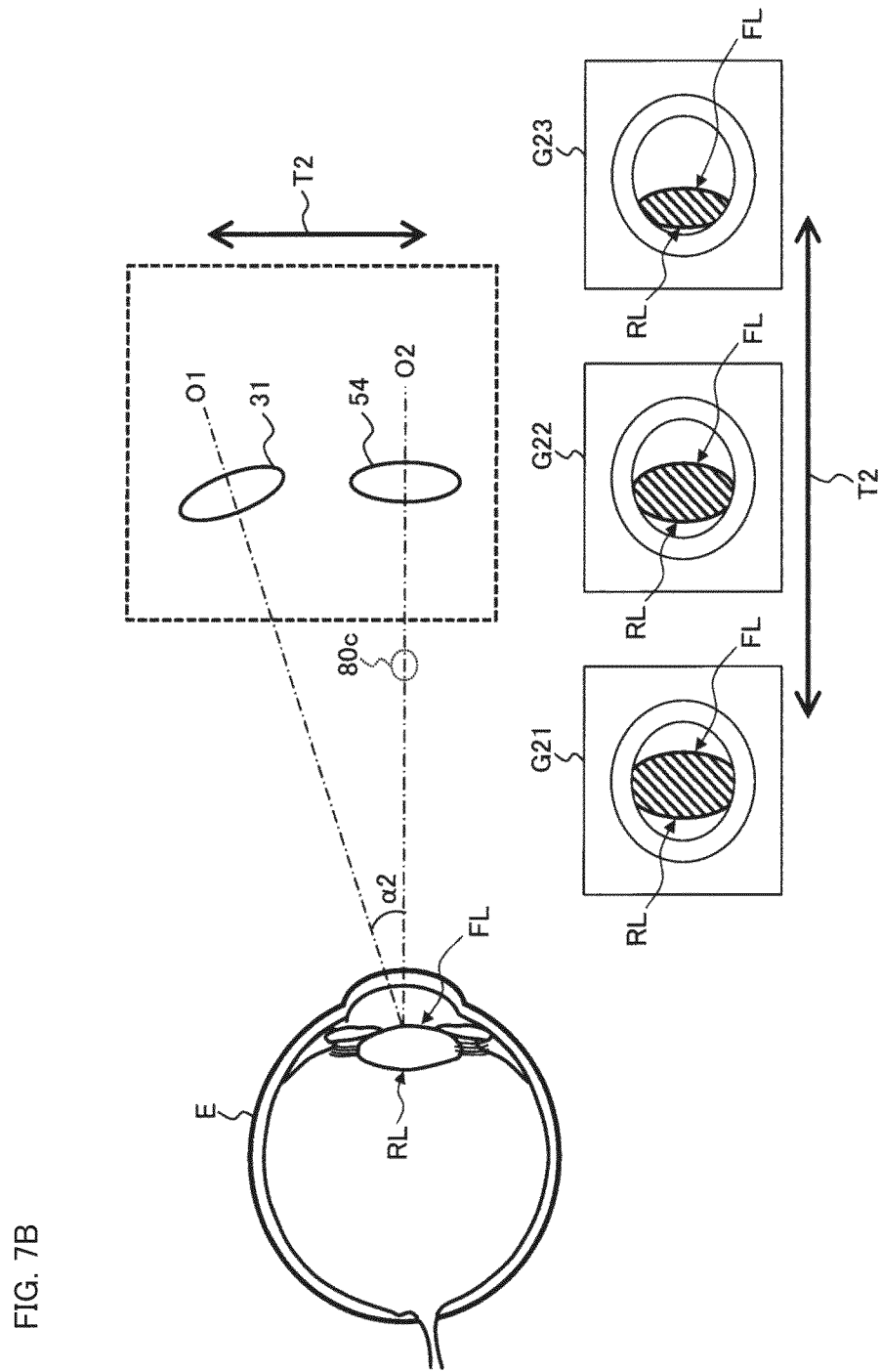
FIG. 7B is a schematic diagram for describing an example of the operation of the slit lamp microscope according to the embodiment example.

FIG. 7B shows another example. In the case of conducting photography by focusing on both the anterior capsule FL and the posterior capsule RL of the crystalline lens, the observation-photographing system 6 may be placed at a position where the photographing angle $\theta_1$=0 degrees (neutral position), and the illumination system 8 may be placed at a position where the illumination angle $\theta_2$=$\alpha 2 \neq 0$ degrees. Here, the illumination angle $\alpha 2$ when focusing on both the anterior capsule FL and the posterior capsule RL is smaller than the illumination angle $\alpha 1$ when focusing on the anterior capsule FL ($\alpha 2 < \alpha 1$).

In such an arrangement state of the optical systems, the scan controller 101B controls the movement mechanism 60 to translate the observation-photographing system 6 and the illumination system 8 together with one another in the +X direction and/or the −X direction (the translation indicated by the arrow T2). The present example may also employ the fixation light source 80c that substantially coincides with the neutral position.

In parallel with such control of the movement mechanism 60, the scan controller 101B executes control of the observation-photographing system 6 to perform photography a plurality of times. This photography control is conducted in the same manner as in the case of focusing on the anterior capsule FL.

With this, photography may be conducted a plurality of times while relatively moving the observation-photographing system 6 and the illumination system 8 with respect to the subject's eye E. The images G21, G22, and G23 illustrated in FIG. 7B schematically show some of a plurality of images acquired by the control of the present example. The depiction position of the crystalline lens (the depiction positions of the anterior capsule FL and the posterior capsule RL) changes corresponding to the translation indicated by the arrow T2, as shown in the images G21 to G23. In this way, a plurality of images corresponding to a plurality of cross sections (a plurality of cross sections arranged in the X direction) of the crystalline lens (the anterior capsule FL and the posterior capsule RL) are acquired.

The present embodiment may carry out anterior segment photography without scanning. For example, photography may be conducted in the state where the observation-photographing system 6 and the illumination system 8 are disposed in such a way that their positions are mutually opposite with respect to the neutral position and their angles against the neutral position are the same. An example of such optical system disposition is shown in FIG. 7C. In this example, $\theta_1$=$-\theta_2$ and abs($\theta_1$)=abs($\theta_2$)=a3$\neq$0.

By performing photography with such an arrangement state of the optical systems, the fine structure of the cornea C of the subject's eye E can be captured as an image. Typically, an image of corneal endothelial cells such as the image G31 may be acquired as in the case of using a specular microscope.

In parallel with the scanning (i.e., acquiring a plurality of cross sectional images) by the movement (rotation, translation) of the optical systems, anterior segment photography may be carried out using the anterior segment camera 70. The anterior segment photography may be a plurality of times of photographing or acquisition of a moving image. Such anterior segment photography makes it possible to detect the movement, motion, change, etc. of the anterior segment during scanning and to perform tracking. Anterior segment photography may be performed during scanning is not being performed.

A scan position (cross sectional position) may be presented together with a front image of the anterior segment acquired by the anterior segment camera 70. For example, an image representing the scan position can be displayed on the front image. Some examples of this can determine a relative position between the front image and the scan position, based on the position of the anterior segment camera 70 (known) and an output from the scan position detector 160.

The memory 102 stores various kinds of computer programs and data. The computer programs include an arithmetic program and a control program for operating the slit lamp microscope 1 according to a predetermined operation mode. The data includes various kinds of data used in various kinds of examinations.

Scan information is an example of such data. For example, the scan information includes the followings: control information for moving the observation-photographing system 6 and the illumination system 8 to a plurality of scan positions of the site of interest; and control information for changing the focal position of the observation-photographing system 6 and that of the illumination system 8 to one or more positions in the depth direction corresponding to scan positions. These pieces of control information are stored in the memory 102 in advance. By using the computer programs and the scan information stored in the memory 102, the controller 101 can perform the control of the scan controller 101B to move the scan position in the horizontal direction and the control of the focus controller 101A to move the focal position, in an individual manner or in an interlocking manner.

The controller 101 includes a processor, a random access memory (RAM), a read only memory (ROM), a hard disk drive, etc. Control programs are stored in advance in a storage such as the ROM and the hard disk drive. The operation of the controller 101 is implemented through cooperation of software such as the control programs and hardware such as the processor. The controller 101 is disposed in the main body of the slit lamp microscope 1 (e.g., inside the base 4) or in the computer 100.

<Image Composition Processor 120>

The image composition processor 120 composes a plurality of cross sectional images acquired by the imaging device 13 according to the above-described control executed by the focus controller 101A and/or the scan controller 101B.

For example, the image composition processor 120 composes a plurality of cross sectional images acquired by the imaging device 13 in parallel with performing the change in the focal position by the focus mechanism 40 and the focus mechanism 50. In this case, the plurality of cross sectional images is arranged in the depth direction. In other words, a plurality of cross sections corresponding to the plurality of cross sectional images is lain in the same plane. A composite image constructed from such a plurality of cross sectional images is a two dimensional cross sectional image with a depth of field that is deeper than those of individual cross sectional images. In other words, such a composite image is a pan-focus (or deep focus) two dimensional cross sectional image.

The image composition processor 120 can compose a plurality of (two dimensional) cross sectional images whose cross sections are not lain in the same plane to construct a three dimensional image. Note that a three dimensional image refers to an image (image data) in which the positions of pixels are defined by a three dimensional coordinate system.

Stack data of a plurality of cross sectional images is an example of three dimensional images. The stack data is image data constructed by arranging a plurality of cross sectional images obtained at a plurality of differing scan positions in a three dimensional manner, based on the positional relationship of the scan positions. More specifically, the stack data is image data constructed by representing a plurality of cross sectional images, which are originally defined by individual two dimensional coordinate systems, by a single three dimensional coordinate system. That is, the stack data is image data constructed by embedding a plurality of cross sectional images in a single three dimensional space.

When constructing stack data from a plurality of cross sectional images acquired by the imaging device 13 in parallel with changing the focal positions by the focus mechanism 40 and the focus mechanism 50, each of the plurality of cross sectional images may be projected onto a cross section lying along the Z direction. For example, cross sectional images photographed at a position where the illumination angle $\theta_2 \neq 0$ degrees may be projected onto a cross section lying along the Z direction (e.g., an XZ cross section or a YZ cross section). Such image projection generates a plurality of projection images parallel to each other. The position of each projection image is determined based on the corresponding cross sectional image. For example, the position of a projection image may be determined such that a predetermined position (e.g., the center position) of the corresponding cross sectional image coincides with a predetermined position (e.g., the center position) of the projection image. Stack data can be constructed by embedding a plurality of projection images, whose respective positions are determined in this manner, in the same three dimensional space.

Volume data is another example of three dimensional images. The volume data is also referred to as voxel data. The volume data is image data in which voxels, which are three dimensional picture elements, are arranged in a three dimensional manner. The volume data is constructed, for example, by applying interpolation to stack data and executing three-dimensionalization (or voxelization) of the pixels of the stack data interpolated.

In order to execute the image composition processing described above, the image composition processor 120 includes the arrangement processor 121 and the composition processor 122.

The arrangement processor 121 can determine an arrangement of a plurality of cross sectional images acquired by an r-scan, a θ-scan (rotation of the optical systems), or a combination of an r-scan and a θ-scan, based on a plurality of pieces of position information (e.g., focal positions, cross sectional positions) associated with the plurality of cross sectional images. The arrangement processor 121, then, can place the plurality of cross sectional images in accordance with the arrangement determined. Alternatively, the arrangement processor 121 can determine an arrangement of a plurality of projection images formed from a plurality of cross sectional images acquired by an r-scan, a θ-scan (rotation of the optical systems), or a combination of an r-scan and a θ-scan, based on a plurality of pieces of position information (e.g., focal positions, cross sectional positions) associated with the plurality of projection images. The arrangement processor 121, then, can place the plurality of projection images in accordance with the arrangement determined.

The arrangement processor 121 can determine an arrangement of a plurality of cross sectional images acquired by a combination of an r-scan and a translation of the optical systems, based on a plurality of pieces of position information (e.g., focal positions, cross sectional positions) associated with the plurality of cross sectional images. The arrangement processor 121, then, can place the plurality of cross sectional images in accordance with the arrangement determined. Alternatively, the arrangement processor 121 can determine an arrangement of a plurality of projection images based on a plurality of cross sectional images acquired by a combination of an r-scan and a translation of the optical systems, based on a plurality of pieces of position information (e.g., focal positions, cross sectional positions) associated with the plurality of projection images. The arrangement processor 121, then, can place the plurality of projection images in accordance with the arrangement determined.

For example, the arrangement processor 121 receives focal positions of slit light detected by the focal position detector 150 (e.g., the position information described above) from the controller 101, and then places a plurality of cross sectional images (or a plurality of projection images) according to the focal positions received. As another example, the arrangement processor 121 receives, from the controller 101, positions of the observation-photographing system 6 and the illumination system 8 detected by the scan position detector 160 (e.g., the position information described above), and then places a plurality of cross sectional images (or a plurality of projection images) according the positions received.

The composition processor 122 composes the plurality of cross sectional images arranged by the arrangement processor 121. This image composition process may include, for example, a process of constructing stack data, and may further include a process of constructing volume data.

By executing a series of processes described above, the image composition processor 120 can construct a three dimensional image or a two dimensional image from a plurality of cross sectional images of the anterior segment of the subject's eye E.

In some other examples, the image composition processor 120 may be configured to compose a plurality of cross sectional images without referring to the position information described above. For example, the image composition processor 120 may be configured to execute the following processes: a process of applying image analysis to a plurality of cross sectional images to identify two or more image regions (referred to as common regions), all of which correspond to the same site in the subject's eye E, in two or more of the plurality of cross sectional images; and a process of composing (or pasting together) the two or more cross sectional images in such a manner that the common regions overlap with each other. In the case where the image analysis described above is applied, the focal position detector 150 and the scan position detector 160 are not required. On the other hand, the image composition processor 120 may be configured to perform rough position adjustment (rough registration) between images with referring to information obtained by the focal position detector 150 and/or the scan position detector 160, and then perform fine position adjustment (fine registration) with image analysis.

At least part of the functions of the image composition processor 120 may be given by an apparatus different from the slit lamp microscope 1. For example, a computer that is capable of communicating with the slit lamp microscope 1 may have at least part of the functions of the image composition processor 120. As a specific example, a computer located in a facility where the slit lamp microscope 1 is installed (e.g., the terminal 3000-n, an intra-facility server) may have at least part of the functions of the image composition processor 120. The management server 4000, or a computer that is capable of communicating with the management server 4000, may have at least part of the functions of the image composition processor 120. The remote terminal 5000m, or a computer that is capable of communicating with the remote terminal 5000m, may have at least part of the functions of the image composition processor 120.

<Focal Position Detector 150>

The focal position detector 150 includes, for example, the first focal position detector and the second focal position detector. The first focal position detector detects the focal position of the observation-photographing system 6, and the second focal position detector detects the focal position of the illumination system 8. The first focal position detector and/or the second focal position detector may include a position sensor such as an encoder or a potentiometer.

In some other examples, the first focal position detector may include a processor that determines the focal position of the observation-photographing system 6 based on the contents of controls executed by the focus controller 101A on the observation-photographing system 6. The contents of controls correspond to the history of controls. Likewise, the second focal position detector may include a processor that determines the focal position of the illumination system 8 based on the contents of controls executed by the focus controller 101A on the illumination system 8 (i.e., the history of controls).

<Scan Position Detector 160>

The scan position detector 160 includes, for example, the first position detector and the second position detector. The first position detector detects the position of the observation-photographing system 6, and the second position detector detects the position of the illumination system 8. The first position detector and/or the second position detector includes, for example, a position sensor that detects the position of the base 4, and a rotation angle sensor that detects the positions of the support arms 16 and 17.

In some other examples, the first position detector may include a processor that determines the position of the observation-photographing system 6 based on the contents of controls (i.e., the history of controls) executed by the scan controller 101B on the observation-photographing system 6. Likewise, the second position detector may include a processor that determines the position of the illumination system 8 based on the contents of controls (i.e., the history of controls) executed by the scan controller 101B on the illumination system 8.

<Display Device 130>

The display device 130 displays various kinds of information under the control of the controller 101. For example, the display device 130 includes a flat panel display such as a liquid crystal display (LCD). The display device 130 may be provided in the main body of the slit lamp microscope 1 or may be provided in the computer 100.

<Operation Device 140>

The operation device 140 includes an operation device for operating the slit lamp microscope 1 and an input device for inputting information. The operation device 140 includes buttons and switches provided in the slit lamp microscope 1 (e.g., the operation handle 5 and the magnification operation knob 11), and operation devices provided in the computer 100 (e.g., a mouse and a keyboard). Further, the operation device 140 may include any kind of operation devices and any kind of input devices, such as a trackball, an operation panel, a switch, a button, and a dial.

The display device 130 and the operation device 140 are shown separately in FIG. 4. On the other hand, at least part of the display device 130 and at least part of the operation device 140 may be a single device. A touch screen is a specific example of such a single device.

<Communication Device 170>

The communication device 170 performs data communication between the slit lamp microscope 1 and another apparatus. The system of the data communication may be arbitrary. For example, the communication device 170 may include any one or more of a communication interface conforming to the Internet, a communication interface conforming to a dedicated line, a communication interface conforming to LAN, and a communication interface conforming to near field communication. The data communication may be either wireless communication or wired communication.

Data sent and received by the communication device 170 may be encrypted. If this is the case, for example, the controller 101 includes an encryptor and a decryptor. The encryptor is configured to encrypt data to be sent. The decryptor is configured to decrypt data having been received.

<Management Server 4000>

Figure 8:
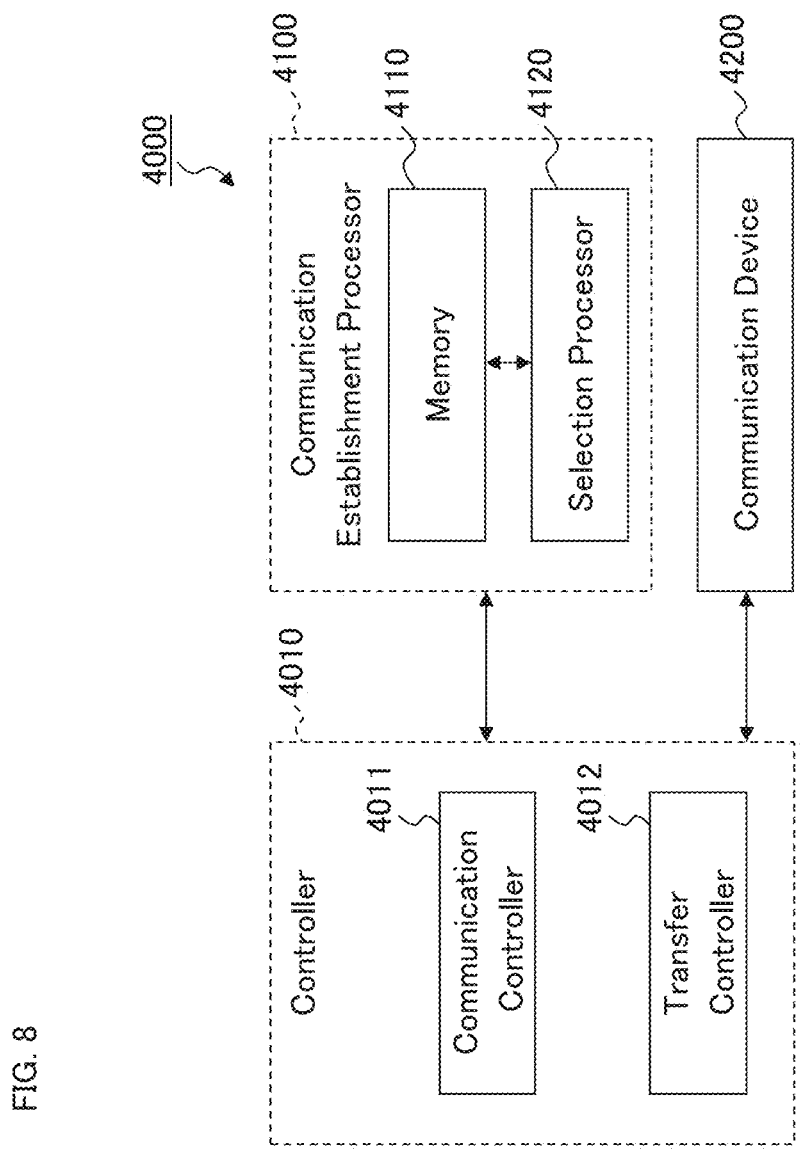
FIG. 8 is a schematic diagram illustrating an example of the configuration of the management server according to the embodiment example.

A description is given of the configuration of the management server 4000. The management server 4000 illustrated in FIG. 8 includes the controller 4010, the communication establishment processor 4100, and the communication device 4200.

<Controller 4010>

The controller 4010 executes control of each part of the management server 4000. The controller 4010 may be capable of executing other processing such as arithmetic processing. The controller 4010 includes a processor. The controller 4010 may further include a RAM, a ROM, a hard disk drive, a solid state drive, etc.

The controller 4010 includes the communication controller 4011 and the transfer controller 4012.

The communication controller 4011 performs control relating to the establishment of communication between a plurality of apparatuses that includes a plurality of ophthalmic imaging apparatus 2000-$i_n$, a plurality of terminals 3000-n, and a plurality of remote terminals 5000m. For example, the communication controller 4011 sends a control signal for establishing communication to each of two or more apparatuses selected by the selection processor 4120 from among a plurality of apparatuses included in the ophthalmic system 1000. The selection processor 4120 will be described later.

The transfer controller 4012 performs control relating to the exchange of information between two or more apparatuses whose communication has been established by the communication establishment processor 4100 (and the communication controller 4011). For example, the transfer controller 4012 functions to transfer information transmitted from one of the at least two apparatuses whose communication has been established by the communication establishment processor 4100 (and the communication controller 4011), to another apparatus.

As a specific example, in the case where the communication between the ophthalmic imaging apparatus $2000\text{-}i_n$ and the remote terminal $5000m$ has been established, the transfer controller 4012 can transfer information transmitted from the ophthalmic imaging apparatus $2000\text{-}i_n$ to the remote terminal $5000m$. The information transmitted from the ophthalmic imaging apparatus $2000\text{-}i_n$ may include an image acquired by the ophthalmic imaging apparatus $2000\text{-}i_n$, information input to the ophthalmic imaging apparatus $2000\text{-}i_n$, or the like. Conversely, the transfer controller 4012 can transfer information transmitted from the remote terminal $5000m$ to the ophthalmic imaging apparatus $2000\text{-}i_n$. The information transmitted from the remote terminal $5000m$ may include the result of the selection of operation mode of the ophthalmic imaging apparatus $2000\text{-}i_n$.

The transfer controller 4012 may have a function of processing information received from another apparatus. If this is the case, the transfer controller 4012 can transmit at least one of the received information and information created using the processing function, to an apparatus that is a destination of transfer.

For example, the transfer controller 4012 can extract part of the information transmitted from an apparatus such as the ophthalmic imaging apparatus $2000\text{-}i_n$, and transmit the extracted information to an apparatus such as the remote terminal $5000m$. Further, the management server 4000 or another apparatus may be configured to analyze information transmitted from an apparatus such as the ophthalmic imaging apparatus $2000\text{-}i_n$. The information to be analyzed is, for example, an image of the subject's eye E. The transfer controller 4012 can send the result of the analysis of the information (and the original information) to an apparatus such as the remote terminal $5000m$.

In the case where a plurality of cross sectional images has been transmitted from the slit lamp microscope 1 (the ophthalmic imaging apparatus $2000\text{-}i_n$), the management server 4000 or another apparatus can construct a three dimensional image (e.g., stack data or volume data) from the plurality of cross sectional images, and the transfer controller 4012 can send the constructed three dimensional image to the remote terminal $5000m$.

In the case where stack data has been transmitted from the slit lamp microscope 1 (the ophthalmic imaging apparatus $2000\text{-}i_n$), the management server 4000 or another apparatus can construct volume data from the stack data, and the transfer controller 4012 can send the constructed volume data to the remote terminal $5000m$.

The data processing executable by the management server 4000 or another apparatus is not limited to the examples described above and may include data processing of any kind.

<Communication Establishment Processor 4100>

The communication establishment processor 4100 performs processing to establish communication between at least two apparatuses selected from among a plurality of apparatuses including a plurality of ophthalmic imaging apparatus $2000\text{-}i_n$, a plurality of terminals $3000\text{-}n$ and a plurality of remote terminals $5000m$. In the present embodiment, "establishing communication" refers to a concept which includes, for example, at least one of the followings: (1) establishing unidirectional communication from a state in which communication is disconnected; (2) establishing bidirectional communication from a state in which communication is disconnected; (3) switching from a state in which only data reception is possible to a state in which both data reception and data transmission are possible; and (4) switching from a state in which only data transmission is possible to a state in which both data transmission and data reception are possible.

In addition, the communication establishment processor 4100 can perform processing of disconnecting the established communication. In the present embodiment, "disconnecting communication" refers to a concept which includes, for example, at least one of the followings: (1) disconnecting communication from a state in which unidirectional communication has been established; (2) disconnecting communication from a state in which bidirectional communication has been established; (3) switching from a state in which bidirectional communication has been established to unidirectional communication; (4) switching from a state in which data transmission and data reception are possible to a state in which only data reception is possible; and (5) switching from a state in which data transmission and data reception are possible to a state in which only data transmission is possible.

Each of the ophthalmic imaging apparatus $2000\text{-}i_n$, the terminal $3000\text{-}n$, and the remote terminal $5000m$ can send at least one of the following communication requests to the management server 4000: a communication request (a call request) for calling another apparatus or the user thereof; and a communication request (an interruption request) for interrupting communication between two other apparatuses. A call request is issued manually or automatically, and an interrupt request is issued manually or automatically. The management server 4000 (the communication device 4200 therein) receives a communication request transmitted from the ophthalmic imaging apparatus $2000\text{-}i_n$, the terminal $3000\text{-}n$, or the remote terminal $5000m$.

The communication establishment processor 4100 of the present embodiment may include the selection processor 4120. For example, based on a communication request sent from the ophthalmic imaging apparatus $2000\text{-}i_n$, the terminal $3000\text{-}n$, or the remote terminal $5000m$, the selection device 4120 selects one or more apparatuses other than the apparatus that has sent the communication request, from among the ophthalmic imaging apparatus $2000\text{-}i_n$, the terminal $3000\text{-}n$, and the remote terminal $5000m$.

A specific example of the processing executed by the selection processor 4120 will be described. When a communication request sent from the ophthalmic imaging apparatus $2000\text{-}i_n$ or the terminal $3000\text{-}n$ is received (e.g., when a request for interpretation of an image acquired by the ophthalmic imaging apparatus $2000\text{-}i_n$ is received), the selection processor 4120 selects, for example, any apparatus from among the plurality of remote terminals $5000m$. The communication establishment processor 4100 establishes communication between the selected remote terminal 5000$m$, and at least one of the ophthalmic imaging apparatus 2000-$i_n$ and the terminal 3000-$n$.

The apparatus selection in response to a communication request is performed, for example, based on a preset attribute. Examples of the attribute include types of examination (e.g., types of imaging modalities, types of images, types of diseases, types of candidate diseases), the degree of expertise required, the level of skill required, and types of languages. In order to realize the processing according to the present example, the communication establishment processor 4100 may include the memory 411 in which attribute information prepared in advance is stored. Attributes corresponding to the remote terminals 5000$m$ and/or attributes corresponding to the users thereof (doctors) are recorded in the attribute information.

The identification of doctors is carried out using, for example, doctor identifiers (doctor IDs) assigned in advance. Further, the identification of the remote terminals 5000$m$ is carried out using, for example, apparatus identifiers or network addresses. In a typical example, the attribute information includes attributes of each doctor such as the doctor's specialized field (e.g., the department, the specialized disease), the doctor's degree of expertise, the doctor's level of skill, or the types of languages the doctor is able to use.

When the selection processor 4120 refers to the attribute information, a communication request to be sent from the ophthalmic imaging apparatus 2000-$i_n$, the terminal 3000-$n$, or the remote terminal 5000$m$ may include information related to attributes. For example, an interpretation request (i.e., a diagnosis request) to be transmitted from the ophthalmic imaging apparatus 2000-$i_n$ may include any of the followings: (1) information indicating the type of imaging modality; (2) information indicating the type of image; (3) information indicating the name of disease or the name of candidate disease; (4) information indicating the degree of difficulty of interpretation; and (5) information indicating a language(s) the user of the ophthalmic imaging apparatus 2000-$i_n$ and/or the terminal 3000-$n$ uses.

When such an interpretation request is received, the selection processor 4120 can select one of the remote terminals 5000$m$ based on the interpretation request and the attribute information stored in the memory 4110. In this selection processing, the selection processor 4120 checks the information related to the attributes included in the interpretation request against the information recorded in the attribute information stored in the memory 4110. With this, the selection processor 4120 selects, for example, the remote terminal 5000$m$ corresponding to a doctor who satisfies any one of the following attributes: (1) a doctor who is specializing in the concerned imaging modality; (2) a doctor who is specializing in the concerned type of images; (3) a doctor who is specializing in the concerned disease (or the concerned candidate disease); (4) a doctor who is capable of performing interpretation of the concerned level of difficulty; and (5) a doctor who is capable of using the concerned language.

The correspondence between doctors and the remote terminals 5000$m$ is made by, for example, referring to doctor IDs input, at the time of logging in, to the remote terminals 5000$m$ (or to the ophthalmic system 1000).

<Communication Device 4200>

The communication device 4200 performs data communication with another apparatus. The another apparatus is, for example, any of the ophthalmic imaging apparatus 2000-$i_n$, the terminal 3000-$n$, and the remote terminal 5000$m$. The system of the data communication and encryption may be performed in the same manner as in the communication device 170 of the ophthalmic imaging apparatus 2000-$i_n$.

<Remote Terminal 5000$m$>

Figure 9:
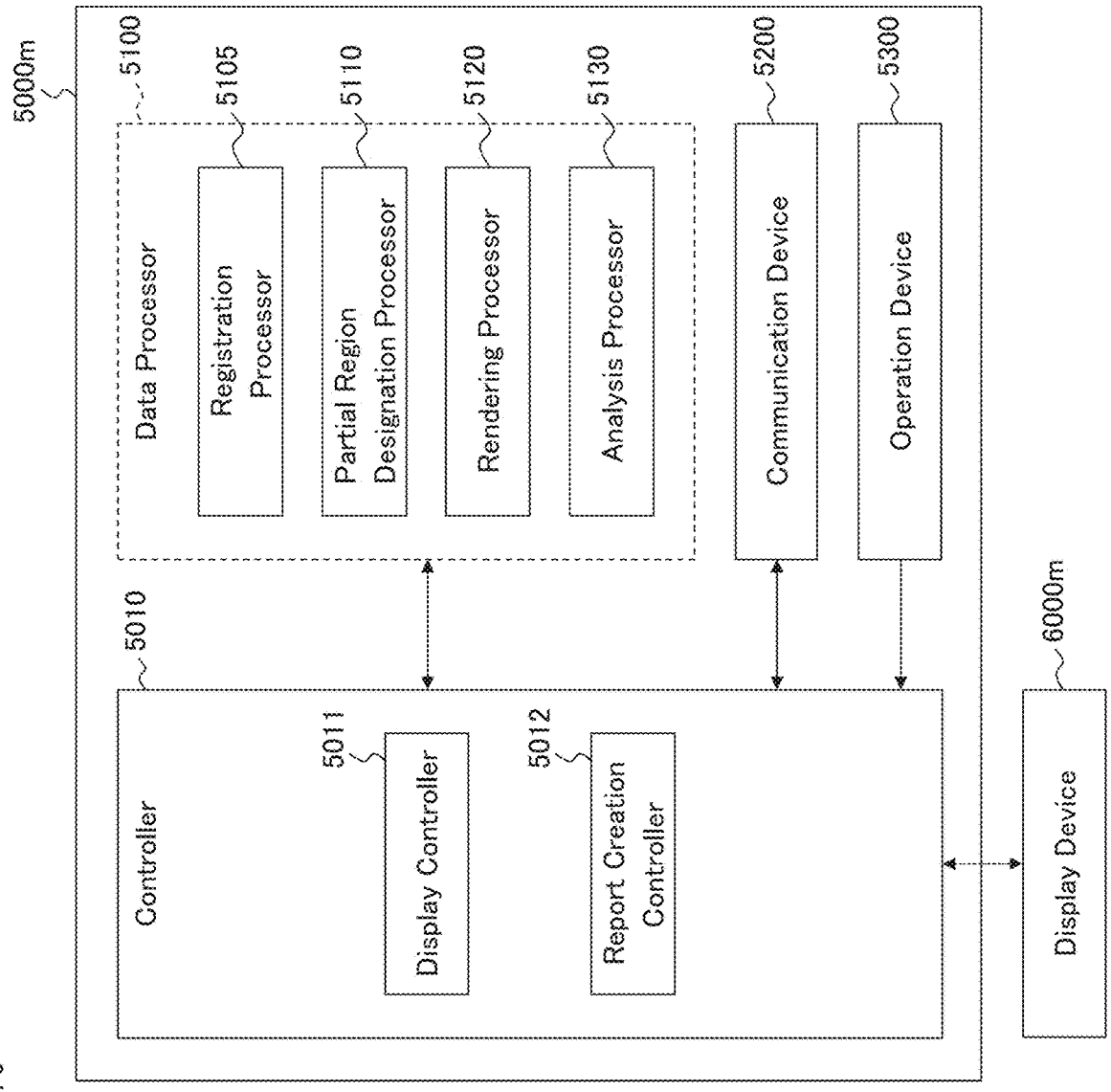
FIG. 9 is a schematic diagram illustrating an example of the configuration of the remote terminal according to the embodiment example.

A description is given of the configuration of the remote terminal 5000$m$. The remote terminal 5000$m$ illustrated in FIG. 9 includes the controller 5010, the data processor 5100, the communication device 5200, and the operation device 5300.

<Controller 5010>

The controller 5010 executes control of each part of the remote terminal 5000$m$. The controller 5010 may be capable of executing other processing such as arithmetic processing. The controller 5010 includes a processor, a RAM, a ROM, a hard disk drive, a solid state drive, etc.

The controller 5010 includes the display controller 5011. The display controller 5011 controls the display device 6000$m$. The display device 6000$m$ may be included in the remote terminal 5000$m$ or may be a peripheral device connected to the remote terminal 5000$m$. The display controller 5011 controls the display device 6000$m$ to display an image of the anterior segment of the subject's eye E. Examples of the image of the anterior segment include a rendered image of a three dimensional image, a front image (or an image photographed from an oblique direction), an OCT image, an image representing an analysis result, and a slit image.

The controller 5010 includes the report creation controller 5012. The report creation controller 5012 executes various kinds of controls for creating a report regarding the information displayed by the display controller 5011. For example, the report creation controller 5012 controls the display device 6000$m$ to display a screen and a graphical user interface (GUI) used for report creation. Further, the report creation controller 5012 inputs or records, into or on a predetermined report template, information input by the user, an image of the anterior segment, analysis data of an image, and the like.

<Data Processor 5100>

The data processor 5100 executes various kinds of data processing.

For example, the data processor 5100 may be configured to construct a three dimensional image (e.g., stack data or volume data) from a plurality of cross sectional images sent from the slit lamp microscope 1 (the ophthalmic imaging apparatus 2000-$i_n$). Further, the data processor 5100 may be configured to construct volume data from stack data sent from the slit lamp microscope 1 (the ophthalmic imaging apparatus 2000-$i_n$).

The data processor 5100 includes the registration processor 5105, the partial region designation processor 5110, the rendering processor 5120, and the analysis processor 5130.

The registration processor 5105 performs registration between a three dimensional image and a front image of the anterior segment. As described above, the relative position between a front image acquired by the anterior segment camera 70 and the position to which a scan is applied (scan position) for three dimensional image acquisition can be determined, based on the position of the anterior segment camera 70 (known) and an output from the scan position detector 160. The registration processor 5105 may perform registration between the three dimensional image and the front image of the anterior segment based on the relative position determined in this way.

In some other examples, the registration processor 5105 may be configured to execute projection of a three dimensional image of the anterior segment in the Z direction to construct a front image (a projection image), and then carry out registration between the projection image and a front image acquired by the anterior segment camera 70. The registration processor 5105 of the present example executes a process of identifying a feature point in a front image acquired by the anterior segment camera 70, a process of identifying a feature point in a projection image, and registration between the front image and the projection image such that the positions of the both feature points coincide with each other. According to the present example, scan position detection is omissible.

The partial region designation processor 5110 executes designation of a partial region of an image (image data) sent from the ophthalmic imaging apparatus 2000-$i_n$, or designation of a partial region of an image displayed based on the sent image data.

Some examples of processing executable by the partial region designation processor 5110 will be described. When a plurality of cross sectional images of the anterior segment of the subject's eye E has been acquired using the slit lamp microscope 1 (the ophthalmic imaging apparatus 2000-$i_n$), a three dimensional image of the anterior segment of the subject's eye E can be constructed by the slit lamp microscope 1, the management server 4000, the remote terminal 5000m, or another apparatus. In the case where such a three dimensional image has been input to the remote terminal 5000m, the controller 5010 may store the three dimensional image in a storage device such as the hard disk drive or the solid state drive mentioned above.

The display controller 5011 can control the display device 6000m to display an image based on the three dimensional image. For example, the controller 5010 sends the three dimensional image (e.g., stack data or volume data) to the rendering processor 5120. The rendering processor 5120 applies rendering to the three dimensional image to construct an image. The display controller 5011 controls the display device 6000m to display the image constructed by the rendering processor 5120.

The user of the remote terminal 5000m (doctor) can designate a partial region of the image displayed on the display device 6000m. The designation operation is performed using the operation device 5300. For example, the user can designate a desired area of the display image using a pointing device.

The partial region designation processor 5110 identifies a partial region of the three dimensional image corresponding to the partial region of the display image designated by the user. Here, the display image is an image obtained by rendering the three dimensional image. Therefore, the partial region of the three dimensional image corresponding to the partial region of the display image is easily identified based on the content of the rendering applied.

Some other examples will be explained. In the case where another image (referred to as a reference image) of the subject's eye E has been acquired in the past, the reference image may be used for designation of a partial region of the three dimensional image. The reference image may be, for example, a front image acquired by the anterior segment camera 70. Alternatively, an OCT image of the anterior segment may be used as the reference image.

At least part of the reference image and at least part of the three dimensional image may depict the same site of the subject's eye E. Alternatively, a wide area image, in which both the site depicted in at least part of the reference image and the site depicted in at least part of the three dimensional image are depicted, can also be further utilized. By using such an image, the registration processor 5105 can perform registration between the reference image and the three dimensional image.

The display controller 5011 can control the display device 6000m to display the reference image (or the wide area image). The user can designate a partial region of the reference image (or a partial region of the wide area image) using the operation device 5300. The partial region designation processor 5110 can designate a partial region of the three dimensional image, based on the partial region of the reference image (or a partial region of the wide area image) designated by the user and a result of the registration between the reference image and the three dimensional image mentioned above.

Thus far, an example of the designation of a partial region of a three dimensional image by a user's operation has been described. However, methods of manual designation are not limited thereto. On the other hand, the partial region designation processor 5110 may be configured to perform automatic designation of a partial region of the three dimensional image, regardless of the user's operation. The automatic designation may be executed using an artificial intelligence processor (cognitive computing processor).

In one example, the partial region designation processor 5110 may be configured to designate a partial region of a three dimensional image, by analyzing a front image of the anterior segment, or by analyzing at least one of the three dimensional image and a display image formed from the three dimensional image. For example, the partial region designation processor 5110 may be configured to identify an image region corresponding to a predetermined tissue of the subject's eye E by applying segmentation to the three dimensional image or the display image, and designate a partial region based on the image region identified. The predetermined tissue of the subject's eye E can be determined, for example, according to arbitrary conditions. Examples of the conditions include the types of imaging modalities, the types of images, and the disease names (the candidate disease names).

The rendering processor 5120 is configured to apply rendering to an image. For example, the rendering processor 5120 carries out rendering of a three dimensional image based on a partial region of the three dimensional image designated by the partial region designation processor 5110.

Methods of the rendering may be arbitrary. For example, the rendering may include three dimensional computer graphics. Three dimensional computer graphics is an arithmetic processing that creates an image having a stereoscopic effect by converting a virtual three dimensional object (e.g., a three dimensional image such as stack data or volume data) in a three dimensional space defined by a three dimensional coordinate system, into two dimensional information.

Examples of the rendering include the volume rendering method, the maximum intensity projection method (MIP), the minimum intensity projection method (MinIP), the surface rendering method, the multi planar reconstruction method (MPR), the projection image construction, and the shadowgram construction. Further examples of rendering include reproduction of a cross sectional image obtained by the slit lamp microscope 1 and construction of a Scheimpflug image. In addition, the rendering processor 5120 may be capable of performing any processing applied together with such rendering.

The analysis processor 5130 is configured to analyze an image such as a three dimensional image of the anterior segment of subject's eye E, a rendered image thereof, a front image.

The rendering processor 5120 may identify a region corresponding to the cornea (a corneal region) in a three dimensional image of the anterior segment. For example, the rendering processor 5120 can identify a region corresponding to the front surface (the anterior surface) of the cornea. Such a region is referred to as a corneal front surface region. In addition, the rendering processor 5120 can identify a region corresponding to the back surface (the posterior surface) of the cornea. Such a region is referred to as a corneal back surface region. Such image region identification may include any known image processing such as segmentation, edge detection, or thresholding.

If the rendering processor 5120 identifies a corneal front surface region, the analysis processor 5130 may analyze the corneal front surface region to determine the corneal curvature radius. For example, the analysis processor 5130 can calculate the curvature radius at each of one or more representative points of the cornea (e.g., at the corneal apex). The report creation controller 5012 may input or record at least one of the corneal curvature radius obtained by the analysis processor 5130 and information generated therefrom, into or on a report template. Note that examples of the information generated from the corneal curvature radius include identification information (a model number, etc.) of contact lenses.

The analysis processor 5130 may calculate a plurality of curvature radii at a plurality of positions of the cornea based on the corneal front surface region identified by the rendering processor 5120. That is, the analysis processor 5130 may determine a corneal curvature radius distribution. Furthermore, the analysis processor 5130 can determine a deviation distribution that represents the deviation of the corneal curvature radius distribution from a standard distribution created in advance. This processing may include registration between the corneal curvature radius distribution and the standard distribution, and comparison (e.g., taking difference) between values at corresponding positions. The report creation controller 5012 can input or record at least one of the deviation distribution determined by the analysis processor 5130 and information generated therefrom, into or on a report template. Note that examples of the information generated from the deviation distribution include identification information (a model number, etc.) of contact lenses.

The display controller 5011 can control the display device 6000*m* to display the deviation distribution obtained by the analysis processor 5130. When displaying the deviation distribution, the magnitudes of deviations from standard values can be represented by colors. As a result of this, a color map showing the deviation distribution of the corneal curvature radius is displayed. The report creation controller 5012 can input or record such a color map into or on a report.

As described above, the registration processor 5105 can perform registration between a front image acquired by the anterior segment camera 70 and a three dimensional image based on a scan. The display controller 5011 can control the display device 6000*m* to display the front image. The user can designate a region of interest in the displayed front image using a user interface such as the operation device 5300. The region of interest is represented, for example, with a line segment indicating a cross section or with an area indicating a three dimensional region. The rendering processor 5120 identifies a partial region of the three dimensional image corresponding to the designated region of interest, based on the result of registration between the front image and the three dimensional image. Further, the rendering processor 5120 constructs a rendered image corresponding to the partial region identified. For example, when a line segment is designated in the front image, the rendering processor 5120 constructs a cross sectional image representing a plane (a cross section) including the line segment designated. When a two dimensional area is designated in the front image, the rendering processor 5120 constructs a rendered image (e.g., a volume rendered image) that represents a three dimensional region that includes the two dimensional area designated.

When the rendering processor 5120 identifies a partial region of a three dimensional image corresponding to a region of interest designated by the user, the display controller 5011 can control the display device 6000*m* to display a rendered image corresponding to the partial region and a front image acquired by the anterior segment camera 70. Further, the display controller 5011 can overlay an image (a rendered region image) representing a region corresponding to the rendered image, on the front image. The rendered region image is, for example, an image representing the position designated by the user with respect to the front image, and is typically an image indicating the position of a line segment or an image indicating the position of the aforementioned two dimensional area.

The rendering processor 5120 can construct a stereoscopic image from a three dimensional image based on a scan. The stereoscopic image may be, for example, a volume rendering image, a surface rendering image, an image representing a three dimensional region identified by segmentation, or the like. The display controller 5011 can control the display device 6000*m* to display the stereoscopic image constructed by the rendering processor 5120. The user can conduct an operation of the stereoscopic image displayed on the display device 6000*m* using a user interface such as the operation device 5300. Examples of the stereoscopic image operation include rotation and change of size (enlargement and reduction). The rotation operation may be a drag operation, for example. The change of size (enlargement and reduction) operation may be, for example, an operation on a GUI (widget) or an operation on a scroll wheel. Further, the user may manipulate the opacity (alpha value) of the stereoscopic image. For example, setting the opacity of a first part of the stereoscopic image to be low allows for the user to observe a second part behind the first part through the transparent first part.

The rendering processor 5120 can identify a crystalline lens region in a three dimensional image based on a scan. This processing includes, for example, segmentation, edge detection, or the like. The analysis processor 5130 can analyze the crystalline lens region identified by the rendering processor 5120 to determine an opacity distribution. This processing includes, for example, thresholding. The opacity of the crystalline lens is seen in cataract eyes and the like. The report creation controller 5012 can input or record at least one of the determined opacity distribution and information generated therefrom, into or on a report template. The opacity distribution is represented as a map, for example. The map representing the opacity distribution may be a color map in which the degrees of opacity are represented by colors. The display controller 5011 can control the display device 6000*m* to display such an opacity distribution (map). Further, the user can arbitrarily rotate the crystalline lens region for better or close observation. Also, the user can observe a desired slice of the crystalline lens region. Furthermore, any analysis, such as thickness measurement or volume measurement, may be applied to the crystalline lens region.

The rendering processor 5120 can identify a vitreous body region in a three dimensional image based on a scan. This processing includes, for example, segmentation, edge detection, or the like. The user can arbitrarily rotate the vitreous body region for better or close observation. Also, the user can observe a desired slice of the vitreous body region. Furthermore, any analysis, such as measurement of the posterior precortical vitreous pocket, may be applied to the vitreous body region.

<Communication Device 5200>

The communication device 5200 performs data communication with another apparatus (e.g., any of the ophthalmic imaging apparatus 2000-$i_n$, the terminal 3000-$n$, and the management server 4000). The system of the data communication and encryption may be performed in the same manner as in the communication device 170 of the ophthalmic imaging apparatus 2000-$i_n$.

<Operation Device 5300>

The operation device 5300 is used to operate the remote terminal 5000$m$ and input information to the remote terminal 5000$m$. In the present embodiment, the operation device 5300 is used to create a report. The operation device 5300 includes an operation device and an input device. The operation device 5300 includes, for example, a mouse, a keyboard, a trackball, an operation panel, a switch, a button, a dial, or the like. The operation device 5300 may include a touch screen.

The operation device 5300 may be used to designate an operation mode of the slit lamp microscope 1. One or more operation modes are provided in advance for the slit lamp microscope 1. A three dimensional imaging mode can be provided in the present embodiment. The three dimensional imaging mode is an operation mode for acquiring three dimensional images of the subject's eye. In the three dimensional imaging mode, the controller 101 of the slit lamp microscope 1 controls the illumination system 8, the observation-photographing system 6, the movement mechanism 60, and the focus mechanisms 40 and 50 in conjunction with one another so that the imaging device 13 acquires a plurality of cross sectional images of the anterior segment of the subject's eye E.

The operation modes of the slit lamp microscope 1 are not limited to the three dimensional imaging mode. For example, any operation mode may be provided corresponding to a site to be imaged or an imaging method such as an anterior capsule imaging mode, an anterior capsule and posterior capsule imaging mode, and a corneal endothelial cell imaging mode.

If the anterior capsule imaging mode is designated, a signal indicating the designation result is transmitted from the remote terminal 5000$m$ to the slit lamp microscope 1 (via the management server 4000). The controller 101 (e.g., the scan controller 101B) of the slit lamp microscope 1 controls the movement mechanism 60 to dispose the observation-photographing system 6 and the illumination system 8 in the state shown in FIG. 7A. As a result, both the observation-photographing system 6 and the illumination system 8 are arranged at their respective initial positions shown in FIG. 7A. By referring to an image acquired in this state, for example, the user of the remote terminal 5000$m$ or the user of the slit lamp microscope 1 may perform adjustment of the position of the observation-photographing system 6 and/or the position of the illumination system 8.

If the anterior capsule and posterior capsule imaging mode is designated, a signal indicating the designation result is transmitted from the remote terminal 5000$m$ to the slit lamp microscope 1 (via the management server 4000). The controller 101 (e.g., the scan controller 101B) of the slit lamp microscope 1 controls the movement mechanism 60 to dispose the observation-photographing system 6 and the illumination system 8 in the state shown in FIG. 7B. As a result, both the observation-photographing system 6 and the illumination system 8 are arranged at their respective initial positions shown in FIG. 7B. By referring to an image acquired in this state, for example, the user of the remote terminal 5000$m$ or the user of the slit lamp microscope 1 may perform adjustment of the position of the observation-photographing system 6 and/or the position of the illumination system 8.

If the corneal endothelial cell imaging mode is designated, a signal indicating the designation result is transmitted from the remote terminal 5000$m$ to the slit lamp microscope 1 (via the management server 4000). The controller 101 (e.g., the scan controller 101B) of the slit lamp microscope 1 controls the movement mechanism 60 to dispose the observation-photographing system 6 and the illumination system 8 in the state shown in FIG. 7C. As a result, both the observation-photographing system 6 and the illumination system 8 are arranged at their respective initial positions shown in FIG. 7C. By referring to an image acquired in this state, for example, the user of the remote terminal 5000$m$ or the user of the slit lamp microscope 1 may perform adjustment of the position of the observation-photographing system 6 and/or the position of the illumination system 8.

In order to implement such operation modes as described above, for example, the memory 102 of the slit lamp microscope 1 stores in advance initial position information in which one or more of initial positions of the observation-photographing system 6 and one or more of initial positions initial position of the illumination system 8 are recorded. The controller 101 (the scan controller 101B) controls the movement mechanism 60 based on the initial position information to move and dispose the observation-photographing system 6 and the illumination system 8 to and at their respective initial positions.

In the present embodiment, for example, the memory 102 stores in advance initial position information corresponding to the anterior capsule imaging mode, initial position information corresponding to the anterior capsule and posterior capsule imaging mode, and initial position information corresponding to the corneal endothelial cell imaging mode. The controller 101 selects and refers to the initial position information corresponding to an operation mode designated.

The initial position information may be stored in advance in the remote terminal 5000$m$ or the management server 4000. If the initial position information is stored in the remote terminal 5000$m$, the remote terminal 5000$m$ may select the initial position information corresponding to an operation mode designated by the user and send the selected initial position information to the slit lamp microscope 1. If the initial position information is stored in the management server 4000, the remote terminal 5000$m$ sends to the management server 4000 a signal indicating the designation result of an operation mode designated by the user. The management server 4000 may select the initial position information corresponding to the signal and send the selected initial position information to the slit lamp microscope 1.

The device used for the designation of an operation mode is not limited to the operation device 5300. For example, the operation mode may be designated using the terminal 3000-$n$ or the operation device 140 of the slit lamp microscope 1. The aspect of the operation mode designation is not limited to such manual designation. For example, an operation mode applied to the concerned subject in the past can be obtained from an electronic medical record or the like and the operation mode applied in the past can be designated. In addition, it is possible to automatically designate an operation mode associated in advance with a specific disease. Further, an operation mode associated in advance with a specific type of examination (e.g., screening, health check, health examination, general examination, medical consultation) can be automatically designated.

<Usage Mode>

Figure 10A:
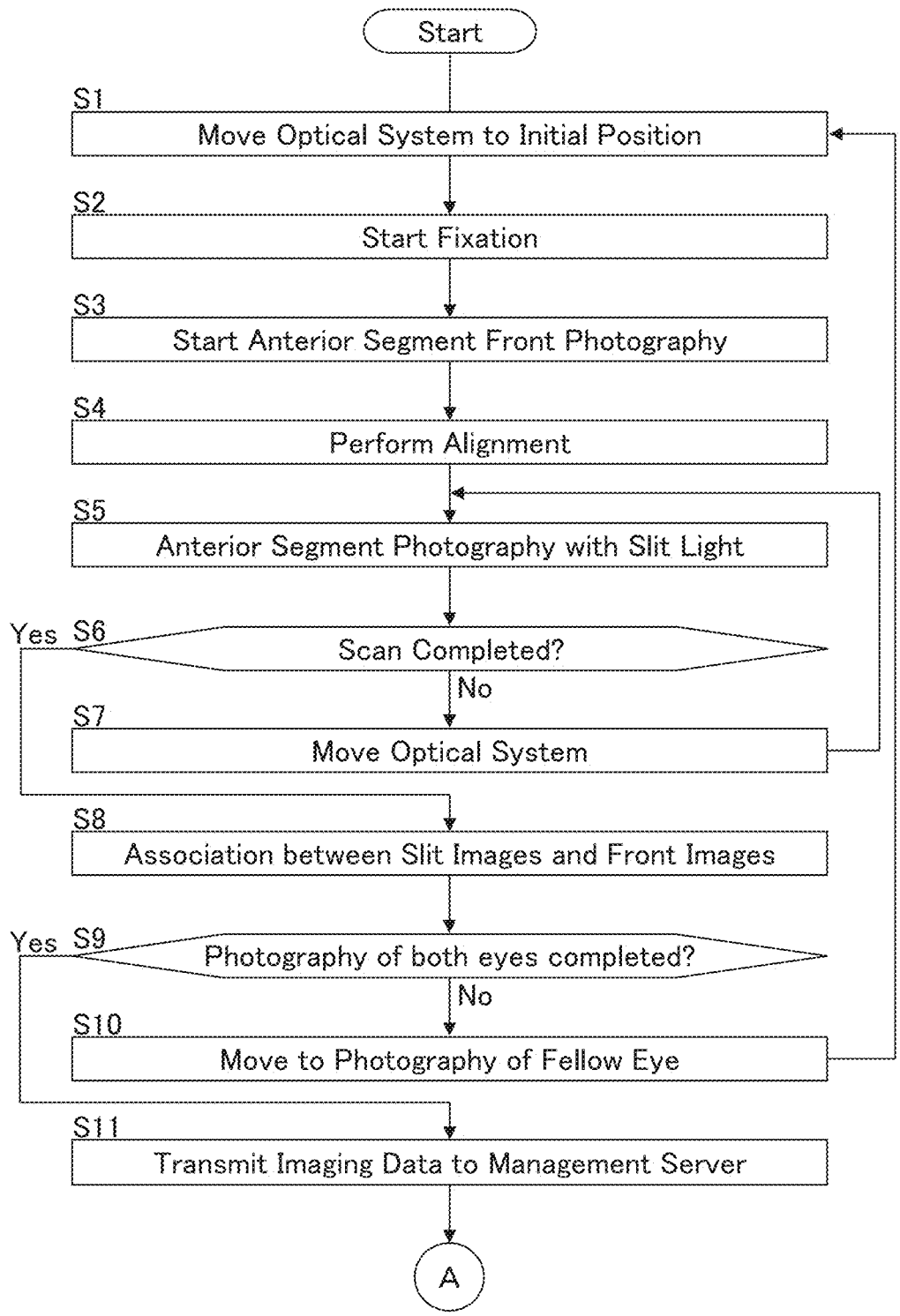
FIG. 10A is a flowchart illustrating an example of the usage mode of the ophthalmic system according to the embodiment example.

The usage mode of the ophthalmic system 1000 according to the present embodiment will be described. FIG. 10A and FIG. 10B show an example of the usage mode of the ophthalmic system 1000. The ophthalmic imaging apparatus 2000-$i_n$ in the present example is the slit lamp microscope 1.

Suppose that the communication between the slit lamp microscope 1 (and/or the terminal 3000-$n$) and the management server 4000 has already been established. Alternatively, the communication between the slit lamp microscope 1 (and/or the terminal 3000-$n$) and the management server 4000 may be established at any timing during the period from the step S1 to the step S11 of FIG. 10A. Further, the communication between the management server 4000 and the remote terminal 5000$m$ has already been established, or is established at any timing during the period from the step S1 of FIG. 10A to the step S13 of FIG. 10B.

As preparation for imaging, subject information is input to the slit lamp microscope 1 (or the terminal 3000-$n$). Referring to FIG. 9A, first, subject information is input to slit lamp microscope 1 (or to the terminal 3000-$n$). The subject information inputted is stored in the memory 102. In the case where communication between the slit lamp microscope 1 (and/or the terminal 3000-$n$) and the management server 4000 has already been established, the subject information inputted may be transmitted to the management server 4000 at this stage. The subject information includes, for example, a subject identifier (subject ID) and background information. The management server 4000 can select one from among the remote terminals 5000$m$ at an arbitrary timing after reception of the subject information.

The subject ID includes, for example, an identifier in a medical facility (a patient identifier), an identifier for a medical check, an identifier for a medical examination, or the like. These are examples only, and the kinds of the subject IDs are not limited to these exemplary IDs.

The background information is any kind of information related to the subject, and examples thereof include information on an medical interview of the subject, information on a sheet filled in by the subject, information on an arbitrary item recorded in the electronic medical record of the subject, an image stored in the subject's account, and the like. Typically, the background information includes the subject's data on items such as gender, age, height, weight, disease name, possible disease name, examination result (e.g., visual acuity value, eye refractive power value, intraocular pressure value), an image (e.g., an OCT image of anterior segment), history of a wearing device for refractive correction (e.g., history of wearing glasses, contact lenses) and the power of the device, examination history, and treatment history. These are examples only, and items of the background information are not limited to them.

For example, the user of the slit lamp microscope 1 (or the user of the terminal 3000-$n$) can input subject information using the operation device 140. In addition, the controller 101 and the communication device 170 may be configured to access an information processing system installed in the facility via a communication path and acquire subject information. Here, the information processing system may include any of a customer management system, an electronic medical record system, and a medical image archiving system. In some aspect examples, subject information may be recorded in a recording medium and read out from it by a data reader. These are examples only, and the methods of inputting subject information are not limited to them.

(S1: Move Optical System to Initial Position)

First, the controller 101 of the slit lamp microscope 1 controls the movement mechanism 60 to dispose the observation-photographing system 6 and the illumination system 8 at their respective initial positions. For example, the observation-photographing system 6 and the illumination system 8 are moved to their respective initial positions in response to the slit lamp microscope 1 being powered on. Alternatively, the observation-photographing system 6 and the illumination system 8 are moved to their respective initial positions in response to the input of the subject ID or the like. As another alternative, the observation-photographing system 6 and the illumination system 8 are moved to their respective initial positions in response to execution of operation mode designation.

(S2: Start Fixation)

Next, the controller 101 controls the fixation system 80 to output fixation light. For example, the controller 101 turns on the fixation light source corresponding to a fixation position designated by the user. Otherwise, the controller 101 receives a result of operation mode designation and turns on the fixation light source associated with the operation mode in advance.

(S3: Start Anterior Segment Front Photography)

Next, the controller 101 controls the anterior segment camera 70 to start the anterior segment photography from the front. For example, the anterior segment camera 70 starts moving image acquisition. If applying the configuration shown in FIG. 3C, at least one of the anterior segment cameras 70$a$ and 70$b$ starts anterior segment photography from an oblique direction(s).

(S4: Perform Alignment)

Next, the slit lamp microscope 1 performs alignment of the observation-photographing system 6 and the illumination system 8 with respect to the subject's eye E by executing one of the procedures described above.

(S5: Anterior Segment Photography with Slit Light)

The controller 101 controls the illumination system 8 to project slit light onto the anterior segment. The observation-photographing system 6 photographs the anterior segment onto which the slit light is being projected. With this, a cross sectional image of the anterior segment is obtained.

(S6: Scan Completed?)

When the scan with the slit light is completed (S6: Yes), the process proceeds to the step S8. When the scanning is not yet completed (S6: No), the process proceeds to the step S7.

For example, the scan consists of a predetermined number of times of photography. Alternatively, an area to which scanning is applied is set in advance. The controller 101 may determine whether or not the scan is completed by referring to such predetermined information. In another example, the controller 101 may determine whether or not the scan is completed based on a user instruction.

(S7: Move Optical System)

If "No" is issued as the determination in the step S6, the controller 101 controls the movement mechanism 60 to move the optical systems. Typically, the observation-photographing system 6 and the illumination system 8 are moved as shown in FIG. 7A and FIG. 7B, for example. The movement is, for example, a translation by a predetermined unit distance or a rotation by a predetermined unit angle.

After the optical systems have been moved, the anterior segment photography is performed using the slit light again (S5). The movement of the optical systems (S7) and the anterior segment photography (S5) are repeatedly executed until "Yes" is issued as the determination in the step S6. Thereby, a plurality of cross sectional images (slit images) corresponding to a plurality of cross sections of the anterior segment are obtained.

Note that the movement of the optical systems is not limited to such stepwise movement. The controller 101 may be configured, in another example, to perform control in the way that photographing is repeated at predetermined time intervals while performing continuous movement of the optical systems.

(S8: Association Between Slit Images and Front Images)

The present example performs slit light scanning in parallel with the moving image acquisition of the anterior segment started in the step S3. With this, a plurality of front images (frames) of the anterior segment and a plurality of slit images are both obtained. The controller 101 may associate the front images and the slit images with each other based on the frame rate (timing of each frame capturing) of the moving image acquisition and the timing of each slit light photography, for example.

Note that the controller 101 may be configured to execute slit light photography and front image acquisition in a synchronous manner. For example, the controller 101 may execute slit light photography and photography with the anterior segment camera 70 at substantially the same timing.

(S9: Photography of Both Eyes Completed?)

When photography of the left eye and photography of the right eye of the subject are both completed (S9: Yes), the process proceeds to the step S11. When photography is completed for only one of the left eye and the right eye (S9: No), the process proceeds to the step S10.

(S10: Move to Photography of Fellow Eye)

If "No" is issued as the determination in the step S9, the process shifts to photography of the opposite eye (the fellow eye) to the one for which photography has already been completed. Then, the steps S1 to S8 are executed for the fellow eye.

(S11: Transmit Imaging Data to Management Server)

If "Yes" is issued as the determination in the step S9, the controller 101 controls the communication device 170 to transmit the data (imaging data) acquired by the photography, to the management server 4000. The imaging data may include subject information, a plurality of slit images, a plurality of front images, correspondence relationships (association) between the slit images and the front images, identification information of the facility (facility ID), and other information.

(S12: Construct Three Dimensional Image)

The communication device 4200 of the management server 4000 receives the imaging data transmitted by the slit lamp microscope 1 in the step S6. The management server 4000 constructs a three dimensional image from the plurality of slit images included in the imaging data.

In the case where the image composition processor 120 of the slit lamp microscope 1 constructs a three dimensional image, imaging data that includes this three dimensional image is sent from the slit lamp microscope 1 to the management server 4000. Similar processes are executed in the case where another apparatus constructs a three dimensional image.

The controller 4010 of the management server 4000 stores the imaging data in a storage such as a hard disk drive or a solid state drive, or in an external database. The data is stored so as to be searchable based on an identifier such as the subject ID and the facility ID.

(S13: Transmit Three Dimensional Image Etc. To Remote Terminal)

The selection processor 4120 selects one of the plurality of remote terminals 5000m. The selection processor 4120 may be configured to perform selection of the remote terminal 5000m by referring to one or more of various kinds of attributes such as types of examination (e.g., types of imaging modalities, types of images, types of diseases, types of possible diseases), degrees of expertise required, levels of skills required, and types of languages, as described above.

The selection processor 4120 may have a function of monitoring the operating status (e.g., information on communication establishment) of each of the remote terminals 5000m. The monitoring function allows the selection processor 4120 to select one of the remote terminals 5000m that is not currently in operation, which may be any of the followings, for example: a terminal that is not currently being used for image interpretation; a terminal that is currently performing image interpretation, but has a flexible schedule or does not have a tight schedule; and a terminal that is not reserved for use in the near future. As a result, the selection processor 4120 can select one of the remote terminals 5000m that is not currently being used for interpretation of other subjects, or the like.

Note that, the monitoring function may be implemented by, for example, managing the operating status of each of the remote terminals 5000m with a flag or the like, based on information inputted from the remote terminals 5000m on a regular basis or non-regular basis, or based on reactions to information transmitted to each of the remote terminals 5000m.

The controller 4010 of the management server 4000 controls the communication device 4200 to transmit the three dimensional image constructed in the step S12, the background information, the front images and the like, to the remote terminal 5000m selected.

(S14: Conduct Interpretation)

The communication device 5200 of the remote terminal 5000m receives the data transmitted from the management server 4000 in the step S13. The controller 5010 stores the received data in the aforementioned storage device. The user of the remote terminal 5000m (e.g., a doctor or an optometrist) can begin medical image interpretation at a desired timing. The user observes the front images of the anterior segment and/or a rendered image of the three dimensional images as desired.

(S15: Create Report)

While performing the interpretation or when the interpretation is completed, the user inputs information obtained by the interpretation and results of diagnosis using the operation device 5300. The report creation controller 5012 creates a report based on information inputted by the user, information selected by the user, and the like.

(S16: Transmit Report to Management Server)

The controller 5010 of the remote terminal 5000m controls the communication device 5200 to transmit the report created in the step S15 to the management server 4000.

(S17: Transmit Report to Facility)

The communication device 4200 of the management server 4000 receives the report transmitted by the remote terminal 5000m in the step S16. The controller 4010 stores the report in a storage such as a hard disk drive or a solid state drive, or in an external database. The report is stored so as to be searchable based on an identifier such as the subject ID and the facility ID.

The controller 4010 searches for the facility in which the anterior segment imaging of the subject has been performed by referring to the search ID, for example. The controller 4010 controls the communication device 4200 to transmit the report to the facility searched. Typically, the controller 4010 transmits the report to the terminal 3000-$n$ installed in the facility searched.

The terminal 3000-$n$ receives the report transmitted by the management server 4000 and displays the report on a display device (not shown in the drawings). The user of the terminal 3000-$n$ explains to the subject the interpretation results, the diagnosis results, a treatment policy, a necessity of a refractive correction device, the options for refractive correction devices, and the like while referring to the report displayed. This is the end of the processes according to the present example.

MODIFICATION EXAMPLES

Some modification examples of the present embodiment will be described. In the above-described embodiment, scanning is performed by moving the slit light in the +X direction and/or the −X direction. Typically, in the scanning, the longitudinal direction of the cross section of the slit light (slit length direction) coincides with the Y direction, and the lateral direction (slit width direction) coincides with the X direction. Such a scan is referred to as a lateral scan.

The orientation of the slit light and the movement direction of the slit light are not limited to the conditions employed in the above-described embodiment. For example, scanning may be performed using slit light whose slit length direction coincides with the X direction and whose slit width direction coincides with the Y direction, and by moving such slit light in the +Y direction and/or the −Y direction. Such a scan is referred to as a vertical scan.

In some embodiment examples, the orientation and the movement direction of slit light may be changeable. For example, a slit lamp microscope of some embodiment examples may be configured to be capable of selection between the lateral scan and the vertical scan. Further, a slit lamp microscope of some embodiment examples may be configured to be capable of changing the orientation and the movement direction of slit light in an arbitrary manner.

Figure 11:
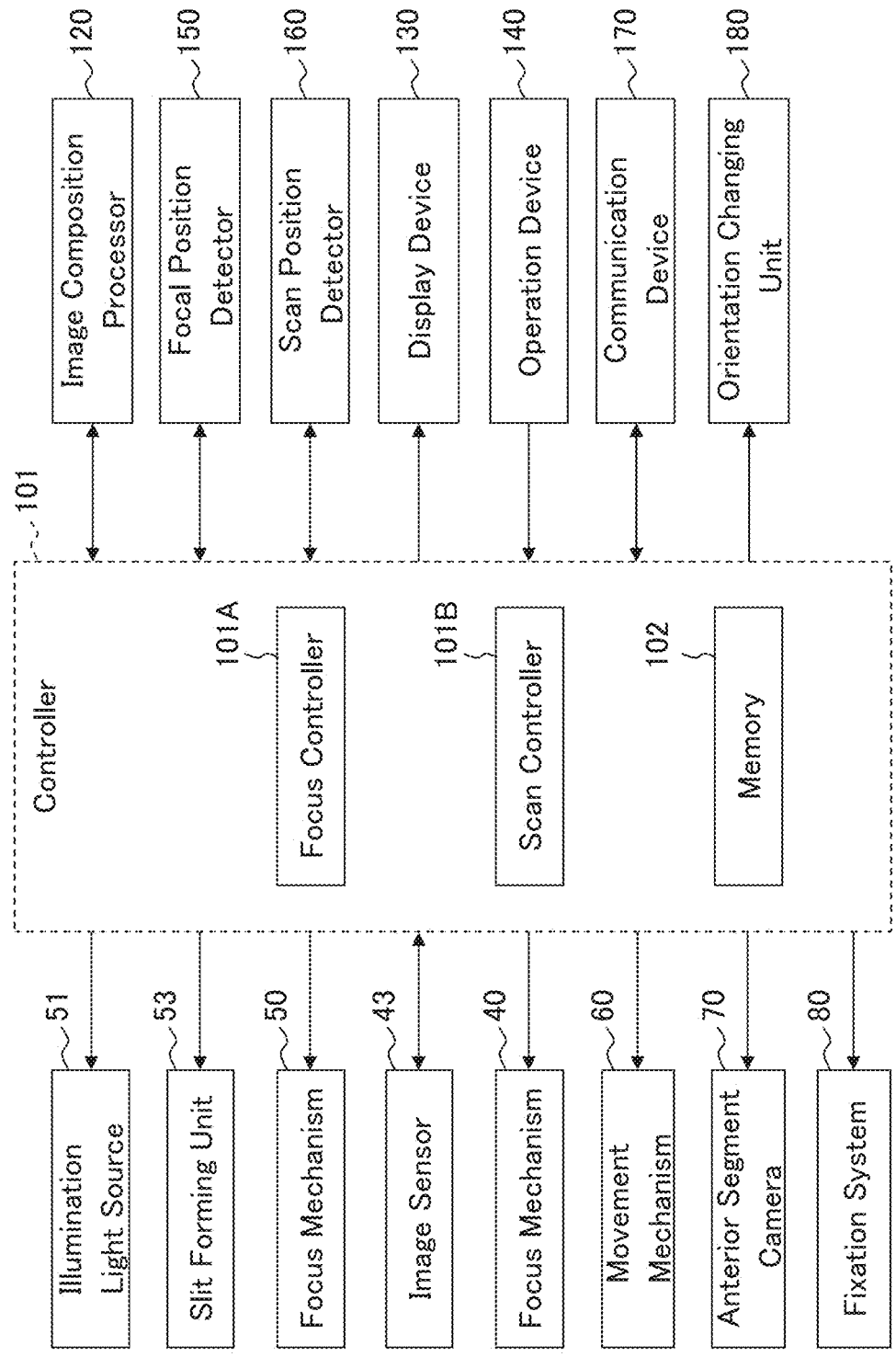
FIG. 11 is a schematic diagram illustrating an example of the configuration of the slit lamp microscope according to the embodiment example.

FIG. 11 shows an example of the configuration of a slit lamp microscope equipped with such functions. The slit lamp microscope of the present example includes the orientation changing unit 180 in addition to the configuration of the above embodiment (FIG. 4). The orientation changing unit 180 is configured to change the orientation of the slit light projected by the illumination system 8. The orientation changing unit 180 may be configured to change the orientation of the slit light by rotating the illumination system 8, for example. The change in the movement direction of the slit light may be implemented by the control of the movement mechanism 60 executed by the controller 101.

<Actions and Effects>

Some actions and effects of the embodiment examples described above will be described.

A slit lamp microscope (1) according to the present embodiment examples includes an illumination system (8), a first photographing system (the observation-photographing system 6), a fixation system (80), a movement mechanism (60), and a controller (101). The illumination system is configured to project slit light onto an anterior segment of a subject's eye from a first direction. The first direction is defined by the optical axis (O2) of the illumination system. The first photographing system is configured to photograph the anterior segment onto which the slit light is being projected, from a second direction different from the first direction. The second direction is defined by the optical axis (O1) of the first photographing system. The fixation system is configured to output fixation light for fixation of the subject's eye. The movement mechanism is configured to be capable of moving the illumination system and the first photographing system. The controller is configured to perform a first control for the movement mechanism to move at least the illumination system and a second control for the first photographing system to photograph the anterior segment a plurality of times in parallel with each other while causing the fixation system to output the fixation light.

According to the slit lamp microscope of the present embodiment examples as described above, the anterior segment can be photographed multiple times while moving the slit light as well as causing the subject's eye to be fixated. Therefore, a plurality of slit images can be acquired through automatic scanning of the anterior segment and thus it becomes unnecessary to have a person operating the slit lamp microscope at the location where the slit lamp microscope is installed. This makes it possible to realize effective and practical use of the slit lamp microscope in telemedicine.

In the present embodiment examples, a controller (101) may perform the first control to move the illumination system (8) and the first photographing system (the observation-photographing system 6) together with each other.

With this, the imaging that focuses on the anterior capsule of the crystalline lens (FIG. 7A) and the imaging that focuses on both the anterior capsule and posterior capsule of the crystalline lens (FIG. 7B) can be conducted in a suitable manner.

The slit lamp microscope (1) according to the present embodiment examples may further include a second photographing system (the anterior segment camera 70) configured to photograph the anterior segment. Further, the controller (101) may be configured to perform a third control for the second photographing system to photograph the anterior segment a plurality of times in parallel with the first control and the second control.

With this, an examiner can grasp the state of the anterior segment when the slit images are acquired.

In the present embodiment examples, the movement mechanism (60) may be capable of moving the illumination system (8) and the first photographing system (the observation-photographing system 6) independently of each other.

This makes it possible to arbitrarily set the relative angle between the illumination system and the first photographing system, that is, the angle formed by the illumination direction (the first direction) and the photographing direction (the second direction). This further contributes to acquisition of a high-quality slit image.

The slit lamp microscope (1) according to the present embodiment examples may further include a memory (102). The memory stores, in advance, initial position information in which an initial position of the illumination system (8) and an initial position of the first photographing system (the observation-photographing system 6) are recorded. Furthermore, the controller (101) may be configured to control the movement mechanism (60) based on the initial position information to place the illumination system and the first photographing system at respective initial positions.

With this, the illumination system and the first photographing system can be easily disposed at their default initial positions. This makes it possible to improve the operability and shorten the duration of imaging time.

In the present embodiment examples, the movement mechanism (60) may be capable of changing at least a movement direction of the illumination system (8) under the first control. For this purpose, the slit lamp microscope (1) of the present embodiment examples may further include an orientation changing unit (180) configured to change an orientation of the slit light projected by the illumination system. Furthermore, at least the movement direction of the illumination system under the first control may be a width direction of a cross section of the slit light (slit width direction).

With such a configuration, it becomes possible to move the slit light in a desired direction to conduct anterior segment imaging (anterior segment scanning) as in the cases of a lateral scan or a vertical scan, for example.

The slit lamp microscope (1) of the present embodiment examples may further include a three dimensional image construction unit (the image composition processor 120) configured to construct a three dimensional image based on a plurality of images (a plurality of slit images) acquired by the first photographing system (the observation-photographing system 6) under the second control.

This makes it possible to construct a three dimensional image such as stack data and volume data from a plurality of slit images. Further, it becomes possible to arbitrarily perform rendering on the three dimensional image.

The slit lamp microscope (1) of the present embodiment examples may further include a communication device (170) configured to transmit a plurality of images (a plurality of slit images) acquired by the first photographing system (the observation-photographing system 6) under the second control, to an information processing apparatus (the management server 4000, the remote terminal 5000*m*, or the like) via a communication path (1100).

Such a configuration makes it possible to process and/or observe a slit image obtained by the slit lamp microscope using the information processing apparatus.

An ophthalmic system (1000) according to the embodiment examples include a slit lamp microscope (1) and an information processing apparatus (the management server 4000, the remote terminal 5000*m*, etc.) connected via a communication path (1100).

The slit lamp microscope includes an illumination system (8), a photographing system (the observation-photographing system 6), a fixation system (80), a movement mechanism (60), a controller (101), and a first communication device (170). The illumination system is configured to project slit light onto an anterior segment of a subject's eye from a first direction. The first direction is defined by the optical axis (O2) of the illumination system. The photographing system is configured to photograph the anterior segment onto which the slit light is being projected, from a second direction different from the first direction. The second direction is defined by the optical axis (O1) of the photographing system. The fixation system is configured to output fixation light for fixation of the subject's eye. The movement mechanism is configured to be capable of moving the illumination system and the photographing system. The controller configured to perform a first control for the movement mechanism to move at least the illumination system and a second control for the photographing system to photograph the anterior segment a plurality of times in parallel with each other while causing the fixation system to output the fixation light. The first communication device is configured to transmit a plurality of images acquired by the photographing system under the second control, to the information processing apparatus via the communication path.

The information processing apparatus includes a second communication device (the communication device 4200, the communication device 5300, etc.) and a three dimensional image construction unit. The second communication device is configured to receive the plurality of images transmitted by the first communication device of the slit lamp microscope. The three dimensional image construction unit is configured to construct a three dimensional image based on the plurality of images received by the second communication device.

According to the ophthalmic system of the present embodiment examples as described above, the slit lamp microscope is capable of photographing the anterior segment multiple times while moving the slit light as well as causing the subject's eye to be fixated. Therefore, a plurality of slit images can be acquired through automatic scanning of the anterior segment and thus it becomes unnecessary to have a person operating the slit lamp microscope at the location where the slit lamp microscope is installed. This makes it possible to realize effective and practical use of the slit lamp microscope in telemedicine. Further, the information processing apparatus is capable of constructing a three dimensional image such as stack data and volume data from a plurality of slit images. Furthermore, it becomes possible to arbitrarily perform rendering on the three dimensional image.

The embodiments described above are merely typical aspect examples of the implementation of the present invention. Therefore, any modifications (e.g., omission, substitution, replacement, addition, etc.) may be made within the scope of the present disclosure.

What is claimed is:

1. A slit lamp microscope comprising:
   an illumination system including an illumination light source and configured to project slit light onto an anterior segment of a subject's eye from a first direction;
   a first photographing system including a lens and configured to photograph the anterior segment onto which the slit light is being projected, from a second direction different from the first direction;
   a second photographing system configured to photograph the anterior segment;
   a fixation system including a fixation light source and configured to output fixation light for fixation of the subject's eye;
   a movement mechanism including an actuator and configured to be capable of moving the illumination system and the first photographing system; and
   a controller circuit configured to perform a first control for the movement mechanism to move at least the illumination system, a second control for the first photographing system to photograph the anterior segment a plurality of times in parallel with each other while causing the fixation system to output the fixation light, and a third control for the second photographing system to photograph the anterior segment a plurality of times in parallel with the first control and the second control.

2. The slit lamp microscope of claim 1, wherein the controller circuit performs the first control to move the illumination system and the first photographing system together with each other.

3. The slit lamp microscope of claim 1, wherein the movement mechanism is capable of moving the illumination system and the first photographing system independently of each other.

4. The slit lamp microscope of claim 1, further comprising a memory that stores, in advance, initial position information in which an initial position of the illumination system and an initial position of the first photographing system are recorded,
   wherein the controller circuit controls the movement mechanism based on the initial position information to place the illumination system and the first photographing system at respective initial positions.

5. The slit lamp microscope of claim 1, wherein the movement mechanism is capable of changing at least a movement direction of the illumination system under the first control.

6. The slit lamp microscope of claim 5, further comprising an orientation changing circuit configured to change an orientation of the slit light projected by the illumination system,
   wherein at least the movement direction of the illumination system under the first control is a width direction of a cross section of the slit light.

7. The slit lamp microscope of claim 1, further comprising a three dimensional image construction circuit configured to construct a three dimensional image based on a plurality of images acquired by the first photographing system under the second control.

8. The slit lamp microscope of claim 1, further comprising a transmitter configured to transmit a plurality of images acquired by the first photographing system under the second control to an information processing apparatus via a communication path.

* * * * *